(12) United States Patent
Alshaer et al.

(10) Patent No.: US 9,232,910 B2
(45) Date of Patent: Jan. 12, 2016

(54) METHOD AND APPARATUS FOR MONITORING BREATHING CYCLE BY FREQUENCY ANALYSIS OF AN ACOUSTIC DATA STREAM

(75) Inventors: Hisham Alshaer, Mississauga (CA); Geoffrey Roy Fernie, Etobicoke (CA); T. Douglas Bradley, Toronto (CA)

(73) Assignee: UNIVERSITY HEALTH NETWORK, Toronto (CA)

( * ) Notice: Subject to any disclaimer, the term of this patent is extended or adjusted under 35 U.S.C. 154(b) by 1113 days.

(21) Appl. No.: 13/129,629

(22) PCT Filed: Nov. 16, 2009

(86) PCT No.: PCT/CA2009/001644
§ 371 (c)(1),
(2), (4) Date: Aug. 11, 2011

(87) PCT Pub. No.: WO2010/054481
PCT Pub. Date: May 20, 2010

(65) Prior Publication Data
US 2011/0288431 A1 Nov. 24, 2011

Related U.S. Application Data

(60) Provisional application No. 61/193,320, filed on Nov. 17, 2008.

(51) Int. Cl.
*A61B 5/08* (2006.01)
*A61B 5/00* (2006.01)
(Continued)

(52) U.S. Cl.
CPC ............. *A61B 5/0803* (2013.01); *A61B 5/4818* (2013.01); *A61B 7/003* (2013.01);
(Continued)

(58) Field of Classification Search
CPC .............................. A61B 5/087; A61B 5/0803
USPC ................................................. 600/529, 534
See application file for complete search history.

(56) References Cited

U.S. PATENT DOCUMENTS

| 4,648,407 A | 3/1987 | Sackner |
|---|---|---|
| 5,671,733 A | 9/1997 | Raviv et al. |

(Continued)

FOREIGN PATENT DOCUMENTS

| WO | WO 01/15602 | 3/2001 |
|---|---|---|
| WO | WO 01/93743 | 12/2001 |

(Continued)

OTHER PUBLICATIONS

Alshaer et al., "Development and validation of an algorithm for detection of apneas and hyponeas using overnight breath sound recordings," American J. of Resp. Crit. Care Med., vol. 183, Meeting Abstracts A6317, D108 Diagnosis and Management of Sleep Disorders, Poster Discussion Session URL: http://aireem.atsjournals.org/cgi/reprint/183/1meetingabstracts/A6317, (2011).

(Continued)

*Primary Examiner* — Jacqueline Cheng
*Assistant Examiner* — Puya Agahi
(74) *Attorney, Agent, or Firm* — Middleton Reutlinger

(57) ABSTRACT

Disclosed herein is a method and apparatus for monitoring, identifying and determining the breathing cycle of an individual from processed acoustic signal waveform data. The breathing sounds of an individual are recorded using a microphone and digitized such that the breathing sounds may be plotted. The data is segmented and transformed to form a plurality of segments representative of a frequency spectrum. The frequency spectrum data is transformed so as to produce magnitude bins and the sum of lower magnitude bins and the sum of higher magnitude bins are determined in a sampling of segments. A Bands Ratio is determined from the sum of lower magnitude bins and the sum of higher magnitude bins in the sampling of segments. A first bands ratio is then determined within a given segment and compared to the mean bands ratio. If the first bands ratio of the given segment is greater than the mean bands ratio by at least a predetermined multiplier, the given segment is labeled as inspiration. If the first bands ratio of the given segment is less than the mean bands ratio by at least a predetermined multiplier, the given segment is labeled as expiration.

36 Claims, 10 Drawing Sheets

(51) Int. Cl.
  *A61B 7/00* (2006.01)
  *A61B 7/04* (2006.01)
  *A61B 5/113* (2006.01)
  *A61B 5/097* (2006.01)

(52) U.S. Cl.
  CPC ...... *A61B 7/04* (2013.01); *A61B 5/097* (2013.01); *A61B 5/1135* (2013.01); *A61B 5/7257* (2013.01); *A61B 2562/0204* (2013.01)

(56) References Cited

U.S. PATENT DOCUMENTS

| | | | |
|---|---|---|---|
| 5,782,240 | A | 7/1998 | Raviv et al. |
| 5,797,852 | A | 8/1998 | Karakasoglu et al. |
| 5,845,636 | A | 12/1998 | Gruenke et al. |
| 5,961,447 | A | 10/1999 | Raviv et al. |
| 6,045,514 | A | 4/2000 | Raviv et al. |
| 6,142,950 | A | 11/2000 | Allen et al. |
| 6,171,258 | B1 | 1/2001 | Karakasoglu et al. |
| 6,213,955 | B1 | 4/2001 | Karakasoglu et al. |
| 6,261,238 | B1* | 7/2001 | Gavriely ................ 600/532 |
| 6,290,654 | B1 | 9/2001 | Karakasoglu |
| 6,368,287 | B1 | 4/2002 | Hadas |
| 6,375,623 | B1 | 4/2002 | Gavriely |
| 7,118,536 | B2 | 10/2006 | Haberland et al. |
| 7,225,021 | B1 | 5/2007 | Park et al. |
| 7,387,124 | B2 | 6/2008 | Noda et al. |
| 7,785,265 | B2 | 8/2010 | Schätzl |
| 7,850,619 | B2 | 12/2010 | Gavish et al. |
| 2002/0123699 | A1 | 9/2002 | Lambert et al. |
| 2005/0222502 | A1 | 10/2005 | Cooper |
| 2006/0196510 | A1 | 9/2006 | McDonald et al. |
| 2008/0243017 | A1 | 10/2008 | Moussavi et al. |
| 2008/0308105 | A1 | 12/2008 | Alder et al. |
| 2008/0319333 | A1 | 12/2008 | Gavish et al. |
| 2009/0118631 | A1 | 5/2009 | Gavish et al. |
| 2009/0293880 | A1 | 12/2009 | Rutan |

FOREIGN PATENT DOCUMENTS

| | | |
|---|---|---|
| WO | 0213697 | 2/2002 |
| WO | 0213938 | 2/2002 |
| WO | 0230280 | 4/2002 |
| WO | 2005096931 | 10/2005 |
| WO | WO 2006/008745 | 1/2006 |
| WO | 2008116318 | 10/2008 |
| WO | WO 2010/054481 | 5/2010 |
| WO | WO 2011/010384 | 1/2011 |
| WO | WO 2012/058727 | 5/2012 |

OTHER PUBLICATIONS

Nakano et al., "Automatic detection of sleep-disordered breathing fro a single-channel airflow record," *European Respiratory Journal*, 29(4): 728-736 (2007).
Varady et al., "A novel method for the detection of apnea and hypopnea events in respiration signals," *IEEE Transactions on Biomedical Engineering*, 49(9): 936-942 (2002).
Werthammer et al., "Apnea monitoring by acoustic detection of airflow," *Pediatrics*, 71(1): 53-55 (1983).
International Search Report issued in application No. PCT/CA2012/000494 (2012).
International Search Report issued in application No. PCT/CA2012/000478 (2012).
Abeyratne et al., "Pitch jump probability measures for the analysis of snoring sounds in apnea," *Physiological Measurement*, vol. 26, pp. 779-798, 2005.
Alshaer et al., "Adaptive segmentation and normalization of breathing acoustic data of subjects with obstructive sleep apnea," Paper presented at: *Science and Technology for Humanity (TIC-STH)*, 2009, *IEEE Toronto International Conference*; Sep. 26-27, 2009.

Alshaer et al., "Phase Tracking of the Breathing Cycle in Sleeping Subjects by Frequency Analysis of Acoustic Data," *International Journal of Healthcare Technology and Management*, vol. 11:3, pp. 163-175 (2010).
Argod, et al., "Differentiating Obstructive and Central Sleep Respiratory Events through Pulse Transit Time," *Am. J. Respir. Crit. Care Med.*, vol. 158:6, pp. 1778-1783 (1998).
Arzt et al., "Association of sleep-disordered breathing and the occurrence of stroke," *Am J Respir Crit Care Med*, vol. 172, pp. 1447-1451 (2005).
Bieger-Farhan et al., "Portable method for the determination of snoring site by sound analysis," Journal of Laryngology & Otology, vol. 118, pp. 135-138 (2004).
Bradley et al., "Sleep apnea and heart failure: Part I: obstructive sleep apnea," Circulation, vol. 107, pp. 1671-1678, Apr. 1, 2003.
Campbell et al., "The perception of wakefulness within sleep," *Sleep*, vol. 4, pp. 177-183 (1981).
Cavusoglu et al., "Investigation of sequential properties of snoring episodes for obstructive sleep apnoea identification," *Physiol Meas.*, vol. 29:8, pp. 879-898 (2008).
Dalmay et al., "Acoustic Properties of the Normal Chest," *Eur. Resp. Jrnl.*, vol. 8, pp. 1761-1769 (1995).
Duckitt et al., "Automatic detection, segmentation and assessment of snoring from ambient acoustic data," *Physiological Measurement*, vol. 27, pp. 1047-1056 (2006).
Fiz et al., "Analysis of forced wheezes in asthma patients," *Respiration*, vol. 73, pp. 55-60, (2006).
Fiz et al., "Detection of wheezing during maximal forced exhalation in patients with obstructed airways," *Chest*, vol. 122, pp. 186-191 (2002).
Fiz et al., "Acoustic analysis of snoring sound in patients with simple snoring and obstructive sleep apnea," *European Respiratory Journal*, vol. 9, pp. 2365-2370 (1996).
Fiz et al., Wheezing identification in asthma subjects during forced exhalation, *American Journal of Respiratory and Critical Care Medicine*, vol. 159, p. A652 (1999).
Folke et al., "Critical review of non-invasive respiratory monitoring in medical care," *Med Biol Eng Comput*, vol. 41, pp. 377-383 (2003).
Fritsch et al., "Monotone piecewise cubic interpolation," *SIAM Journal on Numerical Analysis*, vol. 17, pp. 238-246 (1980).
Gavriely et al., "Parametric representation of normal breath sounds," *J Appl Physiol*, vol. 73:5, pp. 1776-1784 (1992).
Guler et al., "Two-stage classification of respiratory sound patterns," *Comput Biol Med*, vol. 35, pp. 67-83 (2005).
Harrington et al., *Techniques in Speech Acoustics: Kluwer Academic Publisher* (1999).
Hill et al., "Palatal snoring identified by acoustic crest factor analysis," *Physiological Measurement*, vol. 20, pp. 167-174 (1999).
Hoffstein et al., "Snoring: is it in the ear of the beholder?" *Sleep*, vol. 17, pp. 522-626 (1994).
Hult et al., "A bioacoustic method for timing of the different phases of the breathing cycle and monitoring of breathing frequency," *Med Eng Phys*, vol. 22, pp. 425-433 (2000).
Hult et al., "An improved bioacoustic method for monitoring of respiration," *Technol Health Care*, vol. 12, pp. 323-332 (2004).
Jane et al., "Analysis of wheezes in asthmatic patients during spontaneous respiration," *Conf Proc IEEE Eng Med Biol Soc*, vol. 5, p. 3836 (2004).
Jane et al., "Automatic detection of snoring signals: Validation with simple snorers and OSAS patients," *Proceed of the 22nd Annual EMBS Int'l Conf.*, pp. 3129-3130 (2000).
Jane et al., "Automatic snoring signal analysis in sleep studies," *Proceed of the 25th Annual Int'l Conf of the IEEE EMBS*, Cancun, Mexico, pp. 366-369 (2003).
Leung et al., "Sleep apnea and cardiovascular disease," *Am J Respir Crit Care Med*, vol. 164, pp. 2147-2165 (2001).
MacKay, "Information Theory, Inference & Learning Algorithms," Cambridge, UK: *Cambridge University Press*, ch. 20, pp. 284-286 (2003).
Mattei et al., "Diagnosis of sleep apnea," *Minerva Med*, vol. 95, pp. 213-231 (2004).

(56) References Cited

OTHER PUBLICATIONS

Michael et al., "Analysed snoring sounds correlate to obstructive sleep disordered breathing," *European Archives of Oto-Rhino-Laryngology*, vol. 265:1, pp. 105-113 (2008).
Ng et al., "Could formant frequencies of snore signals be an alternative means for the diagnosis of obstructive sleep apnea?" *Sleep Medicine*, vol. 9:8, pp. 894-898 (2008).
Ng et al., "Role of upper airway dimensions in snore production: Acoustical and perceptual findings," *Annals of Biomedical Engineering.*, vol. 37:9, pp. 1807-1817 (2009).
Nieto et al., "Association of sleep-disordered breathing, sleep apnea, and hypertension in a large community-based study. Sleep Heart Health Study," *Jama*, vol. 283, pp. 1829-1836 (2000).
Perez-Padilla et al., "Characteristics of the snoring noise in patients with and without occlusive sleep apnea," *American Review of Respiratory Disease*, vol. 147:3, pp. 635-644 (1993).
Quinn et al., "The differentiation of snoring mechanisms using sound analysis," *Clinical Otolaryngology & Allied Sciences*, vol. 21, pp. 119-123 (1996).
Rabiner et al., "Fundamentals of Speech Recognition," *Prentice Hall*, p. 100-103 (1993).
Radfar et al., "A maximum likelihood estimation of vocal-tract-related filter characteristics for single channel speech separation," *EURASIP Journal on Audio, Speech, and Music Processing*, vol. 2007, Art. ID 84186, pp. 1-15 (2007).
Rechtschaffen et al., "A Manual of Standardized Terminology, Techniques and Scoring System for Sleep Stages of Human Subjects," Los Angeles:*UCLA Brain Information Service/Brain Research Institute* (1968).
Sankur et al., "Comparison of AR-based algorithms for respiratory sounds classification," *Comput Biol Med*, vol. 24, pp. 67-76 (1994).
Sankur et al., "Multiresolution biological transient extraction applied to respiratory crackles," *Comput Biel Med*, vol. 26, pp. 25-39 (1996).
Sen et al., "A multi-channel device for respiratory sound data acquisition and transient detection," *Conf Proc IEEE Eng Med Biol Soc*, vol. 6, pp. 6658-6661 (2005).
Shahar et al., "Sleep-disordered breathing and cardiovascular disease: cross-sectional results of the Sleep Heart Health Study," *Am J Respir Crit Care Med*, vol. 163, pp. 19-25 (2001).
Shiota et al., "Alterations in upper airway cross-sectional area in response to lower body positive pressure in healthy subjects," Thorax, vol. 62, No. 10, pp. 868-872, Oct. 2007.
"Sleep-related breathing disorders in adults: recommendations for syndrome definition and measurement techniques in clinical research," The Report of an American Academy of Sleep Medicine Task Force, *Sleep*. 1999;22(5):667-689.
Sola-Soler et al., "Pitch analysis in snoring signals from simple snorers and patients with obstructive sleep apnea in Engineering in Medicine and Biology," *24th Annual Conf and the Annual Fall Mtg of the Biomedi Engineer Soc, EMBS/BMES Conf. Proceedings of the Second Joint* (2002).
Sola-Soler et al., "Variability of snore parameters in time and frequency domains in snoring subjects with and without Obstructive Sleep Apnea," *Conf Proc IEEE Eng Med Biol Soc*, vol. 3, pp. 2583-2586 (2005).
Steltner et al., "Diagnosis of Sleep Apnea by Automatic Analysis of Nasal Pressure and Forced Oscillation Impedance," *Am. J. Respir. Crit. Care Med.*, vol. 165:7, pp. 940-944 (2002).
Stock et al., "Development and application of a real-time monitoring and feedback system for deep inspiration breath hold based on external marker tracking," *Medical physics.*, vol. 33:8, p. 2868 (2006).
Thomas et al., "Differentiating Obstructive from Central and Complex Sleep Apnea Using an Automated Electrocardiogram-Based Method," *Sleep*, vol. 30:12, pp. 1756-1769 (2007).
Vegfors et al., "Presentation and evaluation of a new optical sensor for respiratory rate monitoring," *Int J Clin Monit Comput*, vol. 11, pp. 151-156 (1994).
Wakwella et al., "Automatic Segmentation and Pitch/Jitter Tracking of Sleep Disturbed Breathing Sounds," *8th International Conf on Control, Automation, Robotics and Vision*, Kunming, China., *IEEE*, p. 936-940 (2004).
Xiong et al., "Problems in Timing of Respiration with the Nasal Thermistor Technique," J Am Soc of Echocardio, vol. 6:2, pp. 210-216 (1993).
Yeginer et al., "Modeling of pulmonary crackles using wavelet networks," *Conf Proc IEEE Eng Med Biol Soc*, vol. 7, pp. 7560-7563 (2005).
Young et al., "The occurrence of sleep-disordered breathing among middle-aged adults," *N Engl J Med*, vol. 328, pp. 1230-1235 (1993).
Young et al., "Estimation of the clinically diagnosed proportion of sleep apnea syndrome in middle-aged men and women," *Sleep*, vol. 20, pp. 705-706 (1997).
Yu et al., "A simple respiration gating technique and its application in high-resolution PET camera," *IEEE Transactions on Nuclear Science*, vol. 52:1, p. 125 (2005).
Int'l Search Report & Written Opinion issued in application No. PCT/CA09/01644 (2010).
International Preliminary Report on Patentability issued in Int'l Patent Application No. PCT/CA2009/001644 (2010).
International Search Report issued in Int'l Patent Application No. PCT/CA2011/000555 (2011).
EP Extended Search Report for EP Application No. EP 09825690.2 (University Health Network) Jan. 15, 2015.
Malmberg, L P., et al. "Changes in Frequency Spectra of Breath Sounds During Histamine Challenge Test in Adult Asthmatics and Healthy Control Subjects." CHEST Journal 105.1 (1994): 122-131.

\* cited by examiner

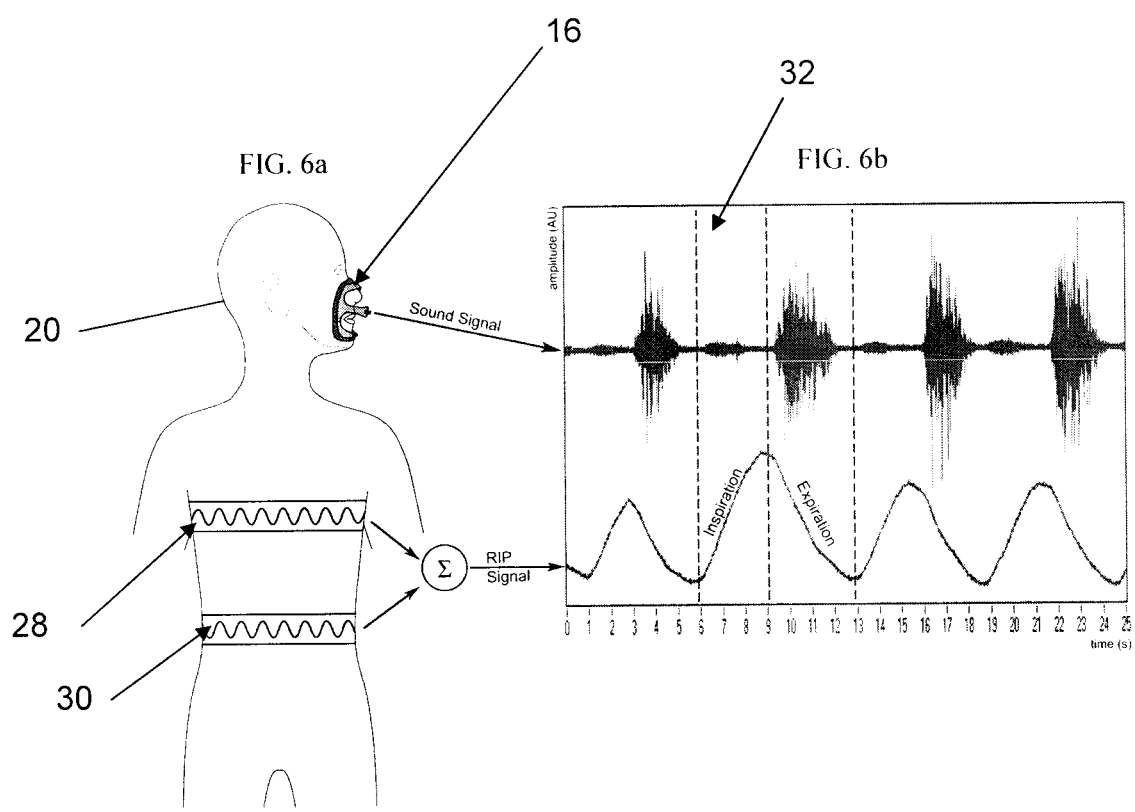

METHOD AND APPARATUS FOR MONITORING BREATHING CYCLE BY FREQUENCY ANALYSIS OF AN ACOUSTIC DATA STREAM

RELATED APPLICATIONS

The present application is a U.S. nationalization under 35 U.S.C. 371 of International Application No. PCT/CA2009/001644, filed Nov. 16, 2009, which claims benefit of priority under 35 U.S.C. §119(e) to U.S. Provisional Patent Application No. 61/193,320, filed Nov. 17, 2008, entitled "TRACKING PHASES OF THE BREATHING CYCLE BY FREQUENCY ANALYSIS OF ACOUSTIC DATA", the disclosures of which i& are hereby fully incorporated herein by reference in their entireties.

FIELD OF THE DISCLOSURE

The present disclosure relates to a method and apparatus for the analysis of breathing cycles and the monitoring, identifying and/or determining the inspiration phase and expiration phase of breathing cycles.

BACKGROUND

Respiratory disorders are known to disturb sleep patterns. For example, recurrent apneas and hypopnea lead to intermittent hypoxia that provokes arousals and fragmentation of sleep, which in turn may lead to restless sleep, and excessive daytime sleepiness. Repetitive apnoeas and intermittent hypoxia may also elicit sympathetic nervous system activation, oxidative stress and elaboration of inflammatory mediators which may cause repetitive surges in blood pressure at night and increase the risk of developing daytime hypertension, atherosclerosis, heart failure, and stroke independently from other risks. There remains a need for improved methods for monitoring, identifying and/or determining breathing cycles, in order to obviate these risks.

SUMMARY OF THE GENERAL INVENTIVE CONCEPT

In an exemplary embodiment, there is provided a method for processing acoustic signal data for use in monitoring the breathing cycle of an individual. The method comprises collecting and generating a data set representative of an acoustic data stream plot of wave amplitude versus time, the data set originating from breathing sounds of an individual and segmenting the acoustic data stream plot into segments wherein each segment spans a predetermined time period. The acoustic data is transformed so as to produce a frequency spectrum in each segment and the frequency spectrum in each segment is transformed so as to produce a plurality of magnitude bins. A sample including a plurality of segments is identified and a sum of lower frequency magnitude bins within a predetermined lower frequency range and a sum of higher frequency magnitude bins within a predetermined higher frequency range are determined. The sum of higher frequency magnitude bins in the sampling is divided by the sum of lower frequency magnitude bins so as to produce a mean bands ratio. A sum of lower frequency magnitude bins and a sum of higher frequency magnitude bins within a given segment is determined and the sum of higher frequency magnitude bins is divided by the sum of lower frequency magnitude bins within said given segment so as to produce a first bands ratio and it is determined whether said first bands ratio is greater or less than said mean bands ratio by at least a predetermined multiplier so as to provide an indication of said breathing cycle.

In some exemplary embodiments, the predetermined multiplier is at least 1. In other exemplary embodiments, the predetermined multiplier is greater than 1.5. In still other exemplary embodiments, the predetermined multiplier is greater than 2.

In some exemplary embodiments, the first bands ratio is labeled as inspiration if the first bands ratio is greater than the mean bands ratio by at least the predetermined multiplier.

In some exemplary embodiments, the first bands ratio is labeled as expiration if the first bands ratio is less than the mean bands ratio by at least the predetermined multiplier.

In some exemplary embodiments, the breathing sounds are collected for a period of time of from about 10 seconds to about 8 hours. In some exemplary embodiments, the breathing sounds are collected for a period of time of from about 10 seconds to about 20 minutes. In some exemplary embodiments, the breathing sounds are collected for a period of time of from about 10 seconds to about 25 seconds. In some exemplary embodiments, the breathing sounds are collected for a period of time of greater than 20 minutes. In some exemplary embodiments, the breathing sounds are collected for a period of time about 25 seconds.

In some exemplary embodiments, each of the segments represents a time period of from about 50 ms to about 1 second. In some exemplary embodiments, each of the segments represents a time period of from about 100 ms to about 500 ms. In some exemplary embodiments, each of the segments represents a time period of about 200 ms.

In some exemplary embodiments, the lower frequency range is from about 0 Hz to about 500 Hz. In some exemplary embodiments, the lower frequency range is from about 10 Hz to about 400 Hz.

In some exemplary embodiments, the higher frequency range is from about 500 Hz to about 25,000 Hz. In some exemplary embodiments, the higher frequency range is from about 400 Hz to about 1,000 Hz.

In some exemplary embodiments, the sampling of the plurality of segments is selected from the recording randomly. In other exemplary embodiments, the sampling of the plurality of segments includes substantially all of the segments in the recording. In still other exemplary embodiments, the mean bands ratio is determined from at least two segments preceding the first bands ratio segment.

In some exemplary embodiments, the method further comprises, before the generating step, recording the breathing sounds with at least one microphone.

In some exemplary embodiments, the audio collecting of breathing sounds of an individual comprises airflow sounds resultant from the individual's breathing applying air pressure to a diaphragm of the microphone. In some exemplary embodiments, the collecting of breathing sounds of an individual comprises breathing sounds resultant from the breathing of the individual being recorded by the microphone. In some exemplary embodiments, the collecting of breathing sounds of an individual comprises airflow sounds resultant from the individual's breathing applying air pressure to a diaphragm of the microphone and actual breathing sounds resultant from the individual being recorded by the microphone.

In some exemplary embodiments, the collection of breathing sounds is digitized in real-time. In some exemplary embodiments, the processing of the collected waveform data is performed in real-time.

In some exemplary embodiments, breathing sounds are collected by at least a first microphone and a second microphone. The first microphone is operable to collect breathing sounds and airflow sounds resultant from the individual's breathing applying air pressure to a diaphragm of the first microphone and the second microphone is operable to collect breathing sounds of the individual. In some exemplary embodiments, the method further comprises, before the generating step, filtering acoustic data of an output representative of second microphone from the acoustic signal data representative of an output of the first microphone so as to provide an acoustic data stream of an audio recording of substantially airflow sounds of the individual.

In some exemplary embodiments, the at least one microphone is provided in a structure including one or more openings of sufficient size to minimize airflow resistance and be substantially devoid of dead space.

In another exemplary embodiment, there is provided an apparatus for transforming acoustic signal data breathing sounds into a graphical representation indicative of breathing cycle phases including inspiration phases and expiration phases. The apparatus comprises at least one microphone for collecting acoustic signal data resultant from the breathing of an individual during a given time period and an acoustic signal data digitizing module for digitizing the acoustic signal data to produce an acoustic data stream plot representative of wave amplitude versus time. At least one processor operable for receiving the acoustic data stream plot is provided. The processor is configured for segmenting the acoustic data stream plot into a plurality of segments of a predetermined length of time, transforming the acoustic data stream in each of the plurality of segments so as to produce a plurality of frequency spectra wherein each frequency spectrum is representative of one of the plurality of segments, transforming each frequency spectrum so as to produce a plurality of magnitude bins in each segment, determining a sum of lower frequency magnitude bins within a predetermined lower frequency range and a sum of higher frequency magnitude bins within a predetermined higher frequency range within a sampling of the plurality segments, dividing the sum of higher frequency magnitude bins by the sum of lower frequency magnitude bins in the sampling so as to produce a mean bands ratio, determining a sum of lower frequency magnitude bins and a sum of higher frequency magnitude bins within a given segment, dividing the sum of higher frequency magnitude bins by the sum of lower frequency magnitude bins within said given segment so as to produce a first bands ratio, comparing said mean bands ratio to said first bands ratio and determining whether said first bands ratio is greater or less than said mean bands ratio by at least a predetermined multiplier so as to determine if said given segment is an inspiration phase or an expiration phase of the breathing cycle. An information relay module in communication with the at least one processor for providing the transformed data to an operator as first indicia representing inspiration and expiration is also provided.

In some exemplary embodiments, the apparatus further comprises a sensor for sensing respiratory movements of an abdomen or rib region of the individual and generating a signal indicative thereof. The processor is operative to receive the signal and to identify respiratory expansion during inspiration and respiratory contraction during expiration. The information relay is operable to provide data to an operator generated as second indicia representing the respiratory movements.

In some exemplary embodiments, the information relay module is provided as a display module for displaying the transformed data as a processed wave amplitude versus time plot. The inspiration phases are identifiable by rising regions of said processed wave amplitude versus time plot and the expiration phases are identifiable by falling regions of said processed wave amplitude versus time plot. In some exemplary embodiments, the information relay module is operable so as to provide an operator audio cues representing the inspiration and expiration phases of an individual's breathing. In some exemplary embodiments, the information relay module is provided as a display module operable for displaying visual cues representing the inspiration and expiration phases of an individual's breathing. In some exemplary embodiments, the information relay module is operable so as to provide an operator printed visual indicia representing the inspiration and expiration phases of an individual's breathing.

In some exemplary embodiments, the breathing sounds are collected by at least a first microphone and a second microphone. The first microphone is operable to collect acoustic signal data breathing sounds and airflow sounds resultant from the individual's breathing applying air pressure to a diaphragm of the first microphone and the second microphone is operable to collect acoustic signal data breathing sounds of the individual. In some exemplary embodiments, the acoustic signal data collected by the second microphone are subtracted from the acoustic signal data collected by the first microphone so as to provide an acoustic signal data recording of substantially airflow sounds of the individual.

In some exemplary embodiments the at least one microphone is provided in a structure including one or more openings sufficient to reduce airflow resistance and be substantially devoid of dead space.

In another exemplary embodiment, there is provided an apparatus for transforming acoustic signal data breathing sounds into a graphical representation indicative of breathing cycle phases including inspiration phases and expiration phases. The apparatus comprises at least one microphone for collecting acoustic signal data resultant from the breathing of an individual during a given time period and an acoustic signal data digitizing module for receiving and digitizing sounds via a transducing link from the at least one microphone. The audio signal digitizing module is operable to produce an acoustic data stream plot representative of wave amplitude versus time. A module for segmenting a plurality of adjacent audio samples from the acoustic data stream plot into a plurality of segments of a predetermined length of time is provided. A module for transforming the acoustic data stream in each of the plurality of segment so as to produce a plurality of frequency spectra wherein each frequency spectrum is representative of one of the plurality of segments is provided. A module for transforming each frequency spectrum so as to produce a plurality of magnitude bins in each segment is provided. A module for determining a sum of lower frequency magnitude bins within a predetermined lower frequency range and a sum of higher frequency magnitude bins within a predetermined higher frequency range within a sampling of the plurality segments is provided. A module for dividing the sum of higher frequency magnitude bins by the sum of lower frequency magnitude bins in the sampling of the plurality of segments so as to produce a mean bands ratio is provided. A module for determining a sum of lower frequency magnitude bins and a sum of higher frequency magnitude bins within a given segment is provided. A module for dividing the sum of higher frequency magnitude bins by the sum of lower frequency magnitude within said given segment so as to produce a first bands ratio is provided. A module for comparing said mean bands ratio to said first bands ratio and determining whether said first bands ratio is greater or less than said mean bands ratio by at least a predetermined multiplier so as to determine if said given segment is an inspiration phase or an expiration phase of the breathing cycle is provided. An information rely module in communication with the module for comparing said mean bands ratio to said first bands ratio for providing the transformed data to an operator as indicia representing inspiration and expiration.

In yet another exemplary embodiment, there is provided a computer implemented apparatus for transforming acoustic signal data breathing sounds into a graphical representation indicative of breathing cycle phases including inspiration phases and expiration phases. The apparatus comprises at least one microphone for collecting acoustic signal data breathing sounds resultant from the breathing of an individual during a given time period and an acoustic signal data digitizing module for receiving and digitizing sounds via a transducing link from the at least one microphone. The audio signal digitizing module is operable to produce an acoustic data stream plot representative of a wave amplitude versus time. At least one processor operable for receiving the acoustic data stream plot is provided. The processor is configured for segmenting a plurality of adjacent audio samples from the acoustic data stream plot into a plurality of segments of a predetermined length of time, transforming the acoustic data stream in each of the plurality of segments so as to produce a plurality of frequency spectra wherein each frequency spectrum is representative of one of the plurality of segments, transforming each frequency spectrum so as to produce a plurality of magnitude bins in each segment, determining a sum of lower frequency magnitude bins within a predetermined lower frequency range and a sum of higher frequency magnitude bins within a predetermined higher frequency range within a sampling of the plurality segments, dividing the sum of higher frequency magnitude bins by the sum of lower frequency magnitude bins in the sampling of the plurality of segments so as to produce a mean bands ratio, determining a sum of lower frequency magnitude bins and a sum of higher frequency magnitude bins within a given segment, dividing the sum of higher frequency magnitude bins by the sum of lower frequency magnitude bins within said given segment so as to produce a first bands ratio, comparing said mean bands ratio to said first bands ratio and determining whether said first bands ratio is greater or less than said mean bands ratio by at least a predetermined multiplier so as to determine if said given segment is an inspiration phase or an expiration phase of the breathing cycle. An information rely module in communication with the at least one processor for providing the transformed data to an operator as indicia representing inspiration and expiration is also provided.

In still another exemplary embodiment, there is provided a method for processing acoustic signal data for use in monitoring a breathing cycle of an individual. The method comprises generating a data set representative of an acoustic data stream plot of wave amplitude versus time. The data set originating from breathing sounds of an individual. The acoustic data stream plot is transformed to yield at least one relatively higher frequency spectral characteristic and at least one relatively lower frequency spectral characteristic. A proportional value of the relatively higher frequency spectral characteristics to the relatively lower frequency spectral characteristics is determined, and least first output indicative of an inspirational breathing phase according to a first range of the proportional value and/or at least one second output indicative of an expirational breathing phase according to a second range of the second proportional value is generated.

In yet another exemplary embodiment, there is provided a device for processing acoustic signal data for use in monitoring a breathing cycle of an individual. The device comprises a means for generating a data set representative of an acoustic data stream plot of wave amplitude versus time. The data set originating from breathing sounds of an individual. Means for transforming the acoustic data stream plot to yield at least one relatively higher frequency spectral characteristic and at least one relatively lower frequency spectral characteristic is provided. Means for determining a proportional value of the relatively higher frequency spectral characteristic to the relatively lower frequency spectral characteristic is provided and means for generating at least first output indicative of an inspirational breathing phase according to a first range of the proportional value and/or at least one second output indicative of an expirational breathing phase according to a second range of the second proportional value is provided.

In still another exemplary embodiment, there is provided a method for processing acoustic signal data for use in monitoring inspirational and expirational phases of a breathing cycle of an individual. The method comprises generating a data set representative of an acoustic data stream plot of wave amplitude versus time. The data set originating from breathing sounds of an individual. The acoustic data stream plot is transformed to yield inspirational spectral data for at least one inspirational phase and expirational spectral data for at least one expirational phase and the shape of the inspirational and expirational frequency spectra for tracking breathing activities is characterized to identify inspirational and expirational breathing phases in subsequent breathing cycles.

In another exemplary embodiment, there is provided a device for processing acoustic signal data for use in monitoring inspirational and expirational phases of a breathing cycle of an individual. The device comprises means for generating a data set representative of an acoustic data stream plot of wave amplitude versus time. The data set originating from breathing sounds of an individual. Means for transforming the acoustic data stream plot to yield inspirational spectral data for at least one inspirational phase and expirational spectral data for at least one expirational phase as provided and means for characterizing the shape of the inspirational and expirational frequency spectra for tracking breathing activities to identify inspirational and expirational breathing phases in subsequent breathing cycles is also provided.

BRIEF DESCRIPTION OF THE FIGURES

Several embodiments of the present disclosure will be provided, by way of examples only, with reference to the appended drawings, wherein:

FIG. 6a is an exemplary set-up of Respiratory Inductance Plethysmogrphy (RIP) on an individual and the microphone and transducer equipment of FIGS. 2a and 2b;

FIG. 6b is an exemplary plot of 25-second long recording of breathing sounds and simultaneous RIP signals from a representative individual wherein the dashed line indicates the separation of inspiration and expiration cycles;

FIG. 7b is a representative frequency spectrum of the inspiration phase of FIG. 7a;

FIG. 7c is a representative frequency spectrum of the expiration phase of FIG. 7a:

DESCRIPTION OF THE PREFERRED EMBODIMENTS

Figure 1:
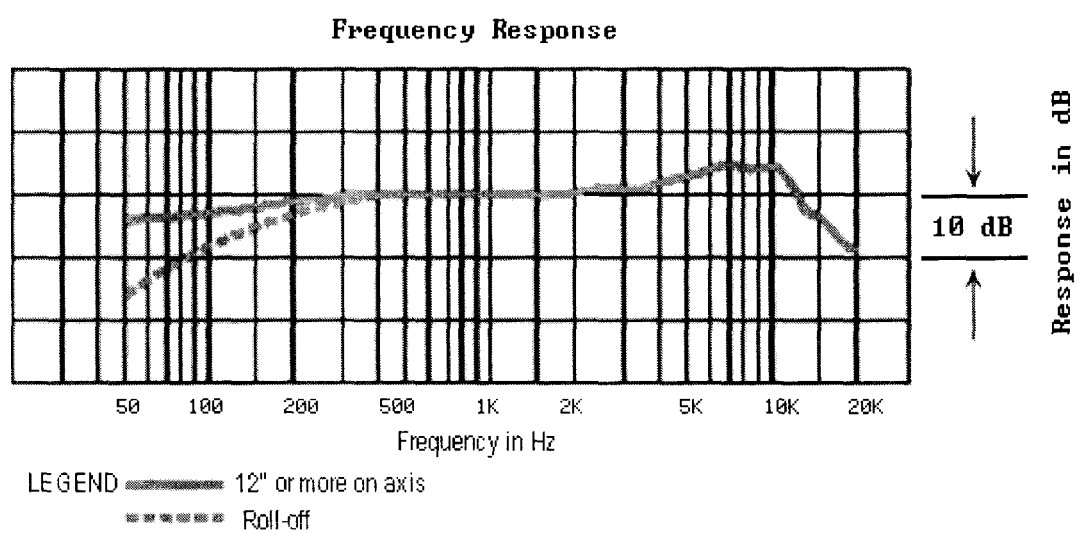
FIG. 1 is a plot of an exemplary microphone response curve of an exemplary embodiment.

It should be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including." "comprising." or "having" and variations thereof herein is meant to encompass the items listed thereafter and equivalents thereof as well as additional items. Unless limited otherwise, the terms "connected," "coupled." and "mounted," and variations thereof herein are used broadly and encompass direct and indirect connections, couplings, and mountings. In addition, the terms "connected" and "coupled" and variations thereof are not restricted to physical or mechanical or electrical connections or couplings. Furthermore, and as described in subsequent paragraphs, the specific mechanical or electrical configurations illustrated in the drawings are intended to exemplify embodiments of the disclosure. However, other alternative mechanical or electrical configurations are possible which are considered to be within the teachings of the instant disclosure. Furthermore, unless otherwise indicated, the term "or" is to be considered inclusive.

With reference to the disclosure herein and the appended figures, a method for monitoring, identifying and/or determining characteristics of an individual's breathing, including breathing phases thereof, is henceforth described using a processed acoustic signal data stream collected and/or recorded waveform data. In one example, the waveform data is collected from or is associated with breathing sounds and other sounds from one or more microphones or other sound wave collecting equivalents thereof.

In this case, the system and method may involve the use of a control unit, in which some or all of its associated components are computer implemented that may be provided in a number of forms. They may be embodied in a software program configured to run on one or more general purpose computers, such as a personal computer, or on a single custom built computer, such as a programmed logic controller (PLC) which is dedicated to the function of the system alone. The system may, alternatively, be executed on a more substantial computer mainframe. The general purpose computer may work within a network involving several general purpose computers, for example those sold under the trade names APPLE or IBM, or clones thereof, which are programmed with operating systems known by the trade names WINDOWS™, LINUX™, MAC O/S™ or other well known or lesser known equivalents of these. The system may involve pre-programmed software using a number of possible languages or a custom designed version of a programming software sold under the trade name ACCESS or other programming software. The computer network may be a wired local area network, or a wide area network such as the Internet, or a combination of the two, with or without added security, authentication protocols, or under "peer-to-peer" or "client-server" or other networking architectures. The network may also be a wireless network or a combination of wired and wireless networks. The wireless network may operate under frequencies such as those dubbed 'radio frequency' or "RF" using protocols such as the 802.11, TCP/IP, BLUE TOOTH and the like, or other well known Internet, wireless, satellite or cell packet protocols. Also, the present method may also be implemented using a microprocessor-based, battery powered device.

Figure 3:
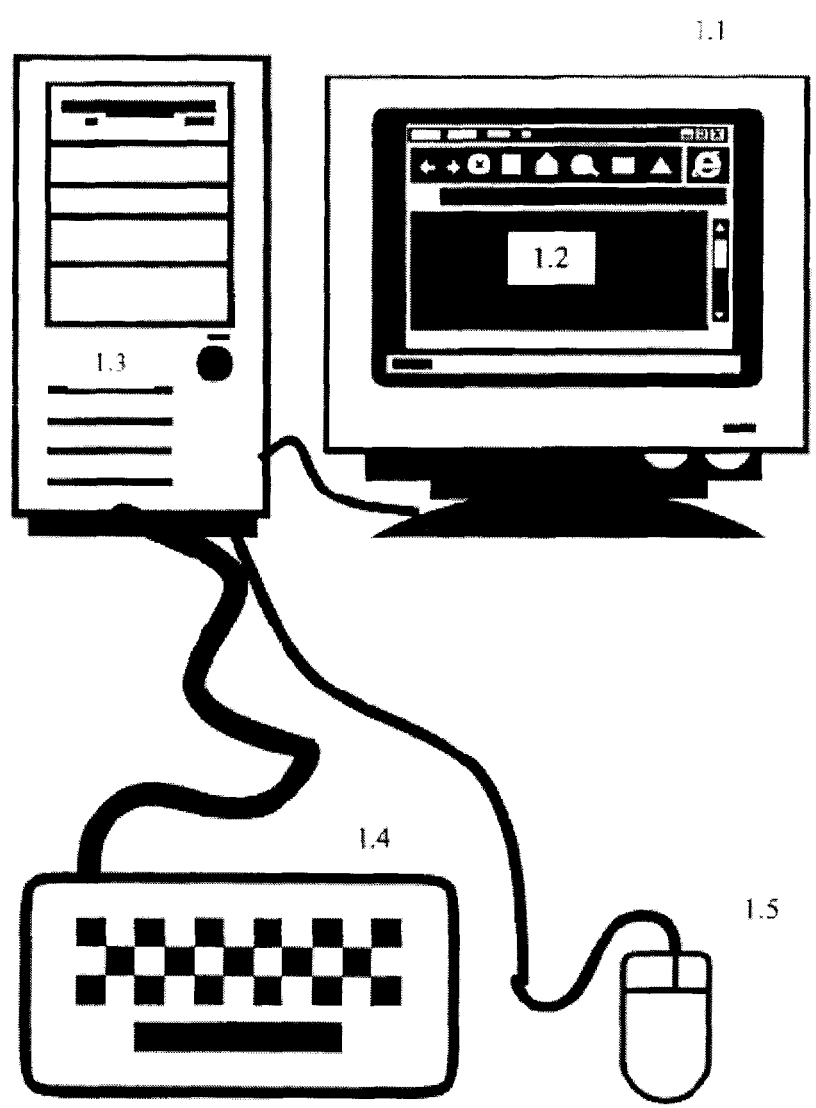
FIG. 3 is a schematic computer system in accordance with an apparatus for transforming breathing sounds in inspiration and expiration phases.

FIG. 3 shows a general computer system on which embodiments may be practiced. The general computer system comprises information relay module (1.1). In some embodiments, the information relay module (1.1) comprises a means for providing audible cues, such as speakers. In some embodiments, the information relay module is comprised of a display device or module (1.1) with a display screen (1.2). Examples of display device are Cathode Ray Tube (CRT) devices, Liquid Crystal Display (LCD) Devices etc. The general computer system can also have other additional output devices like a printer. The cabinet (1.3) houses the additional basic components of the general computer system such as the microprocessor, memory and disk drives. In a general computer system the microprocessor is any commercially available processor of which x86 processors from Intel and 680X0 series from Motorola are examples. Many other microprocessors are available. The general computer system could be a single processor system or may use two or more processors on a single system or over a network. The microprocessor for its functioning uses a volatile memory that is a random access memory such as dynamic random access memory (DRAM) or static memory (SRAM). The disk drives are the permanent storage medium used by the general computer system. This permanent storage could be a magnetic disk, a flash memory and a tape. This storage could be removable like a floppy disk or permanent such as a hard disk. Besides this the cabinet (1.3) can also house other additional components like a Compact Disc Read Only Memory (CD-ROM) drive, sound card, video card etc. The general computer system also includes various input devices such as, for example, a keyboard (1.4) and a mouse (1.5). The keyboard and the mouse are connected to the general computer system through wired or wireless links. The mouse (1.5) could be a two-button mouse, threebutton mouse or a scroll mouse. Besides the said input devices there could be other input devices like a light pen, a track ball, etc. The microprocessor executes a program called the operating system for the basic functioning of the general computer system. The examples of operating systems are UNIX™, WINDOWS™ and OS X™. These operating systems allocate the computer system resources to various programs and help the users to interact with the system. It should be understood that the disclosure is not limited to any particular hardware comprising the computer system or the software running on it.

Figure 4:
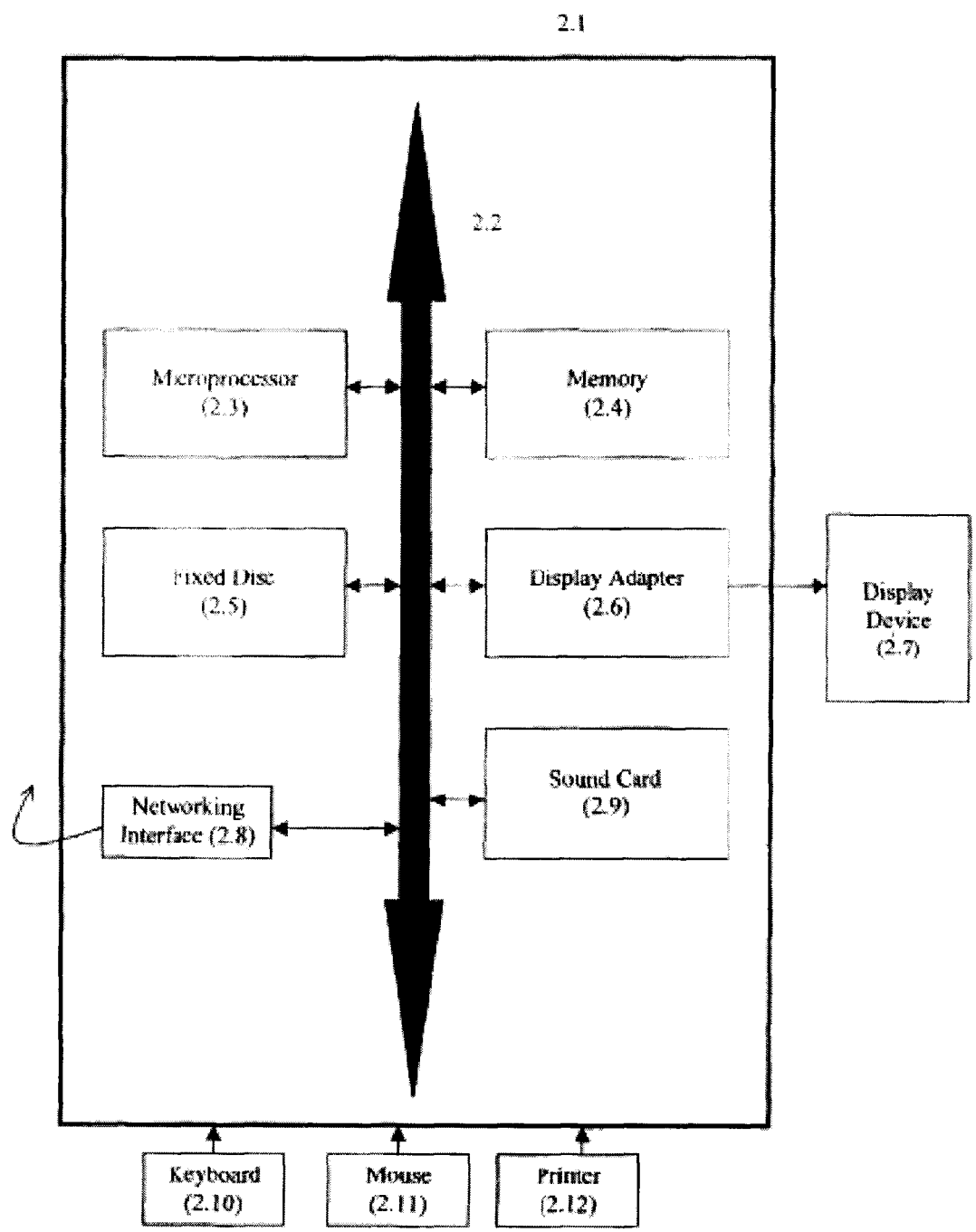
FIG. 4 is a block diagram of a computer system in accordance with the apparatus of FIG. 4.

FIG. 4 shows the internal structure of the general computer system of FIG. 3. The general computer system (2.1) includes various subsystems interconnected with the help of a system bus (2.2). The microprocessor (2.3) communicates and controls the functioning of other subsystems. Memory (2.4) helps the microprocessor in its functioning by storing instructions and data during its execution. Fixed Drive (2.5) is used to hold the data and instructions permanent in nature like the operating system and other programs. Display adapter (2.6) is used as an interface between the system bus and the display device (2.7), which is generally a monitor. The network interface (2.8) is used to connect the computer with other computers on a network through wired or wireless means. The system is connected to various input devices like keyboard (2.10) and mouse (2.11) and output devices like a printer (2.12) or speakers. Various configurations of these subsystems are possible. It should also be noted that a system implementing exemplary embodiments may use less or more number of the subsystems than described above. The computer screen which displays the recommendation results can also be a separate computer system than that which contains components such as database 360 and the other modules described above.

Figure 2A:
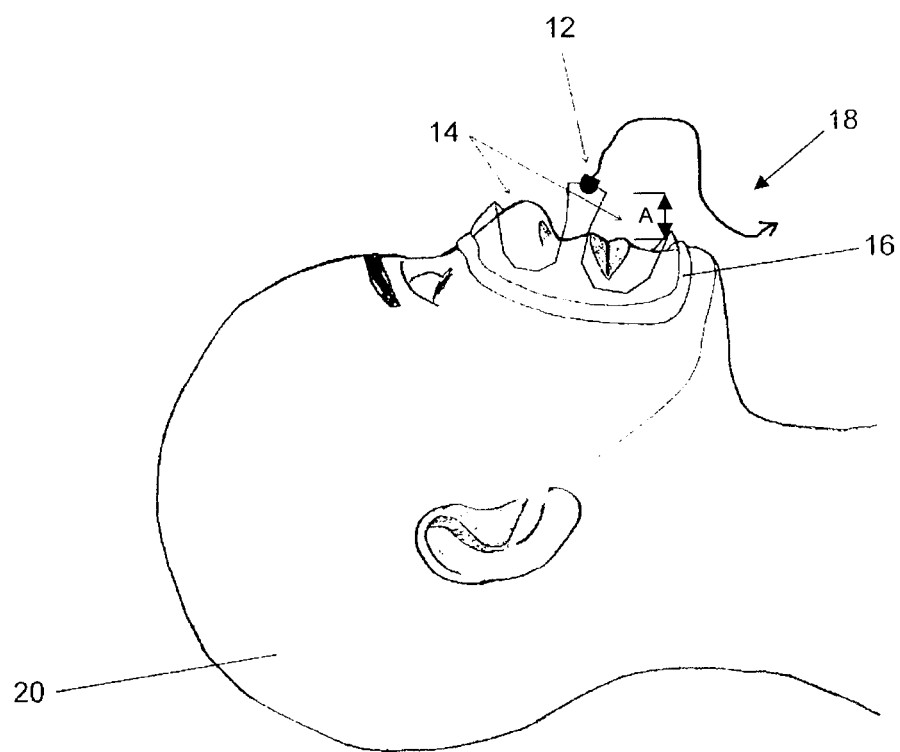
FIG. 2a is side view of an exemplary embodiment of a microphone and transducer set-up on an individual wherein the microphone is attached to a face mask located on the front of an individual's face.
Figure 2B:
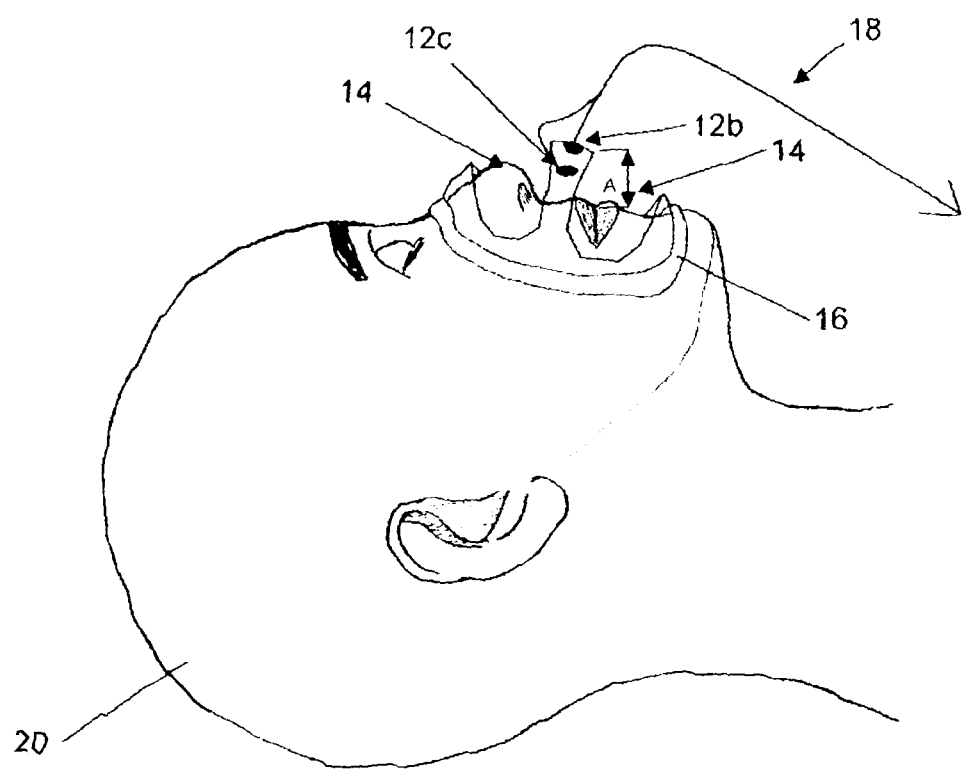
FIG. 2b is side view of an exemplary embodiment of a 2-microphone and transducer set-up on an individual wherein the microphones are attached to a face mask located on the front of an individual's face.

The method, in accordance with the instant disclosure, provides a microphone 12 located in a position proximal to an individual's mouth as shown in FIGS. 2a and 2b, in this case by a dimension A of approximately 3 cm in front of the individual's face. The microphone 12 may be configured to communicate with the microprocessor by way of an interface or other data acquisition system, via a signal transducing link or data path 18 to provide one or more data collection modules with the microphone 12. Thus, such data collection modules and the microphone are operable to collect breathing sounds emanating from the individual's mouth and nose, during the inspiration and/or expiration phases of breathing. For example, an exemplary microphone response curve is shown in FIG. 1. The acoustic signal data breathing sounds collected from the individual may be comprised of both airflow sounds from the individual's breathing applying air pressure to the microphone diaphragm and actual breathing sounds resultant from the individual's breathing being recorded and/or collected by the microphone 12. Furthermore, the acoustic signal data breathing sounds collected from the individual may be, in another exemplary embodiment, comprised of substantially only actual sounds resultant from the individual's breathing being recorded and/or collected by the microphone 12. In still yet another embodiment, the acoustic signal data breathing sounds collected from the individual may be comprised of substantially only airflow sounds resultant from the individual's breathing applying air pressure to the microphone diaphragm and being recorded and/or collected by the microphone 12. As used hereinafter, term "airflow sounds" refers to the air pressure resultant from an individual's breathing being applied to and causing the microphone's diaphragm to move such that the microphone collects and produces data for the audio recording.

The microphone 12, for example, may be coupled in or to a loose fitting full face mask 16 as shown in FIGS. 2a and 2b. Furthermore, the face mask 16 may include at least one opening 14 to allow for ease of breathing of an individual 20. For example, the microphone 12 may be in a fixed location with a spacing of dimension "A", of about 3 cm in front of the individual's face as shown schematically in FIG. 2a; however other distances in front of the individual's face may be desirable in some embodiments. The microphone 12, in this case, is embedded in a respiratory mask 16 which is modified by cutting away material so as produce opening 14 such that only a structural frame portion remains to keep the microphone 12 in a fixed location relative the nostrils and the mouth of an individual 20. In one example, the audio signals from the microphone may be digitized using an audio signal digitizing module and digitized sound data to be transferred via transducing link 18 to the computer using a USB preamplifier and audio interface (M-Audio, Model Fast Track Pro USB) with a sampling rate of 22,050 Hz and resolution of 16 bits. Although various types of audio interfaces may be used, in the instant exemplary embodiment, an external audio interface provides suitable results over the other types of audio adapters, for example, built-in audio adapters due to the superior signal to noise (S/N) ratio of the external adaptor which is about 60 dB at 1 kHz. Sound recordings may then be passed through a order band-stop digital filter with a centre frequency of about 60 Hz to suppress line interference. Other structures may also be used to locate the microphone in position, as including support structures positioned against a plurality of locations on the individual or stationed adjacent the individual as required.

Furthermore, in another exemplary embodiment, a two microphone system may be useful. In such a system, as shown in FIG. 2b, one of the microphones, a first microphone 12b, may be configured to collect actual breathing sounds and airflow sounds whereas the other microphone, a second microphone 12c may be configured to collect substantially only actual breathing sounds. In this embodiment, the waveform sounds and/or data collected from the second microphone 12c may be subtracted or filtered from the waveform sounds collected from the first microphone 12b, thereby resulting in a waveform data stream of substantially only airflow sounds. The airflow sounds may be resultant of pressure air from an individual's breathing being collected as applied to the diaphragm of a microphone as noted above. Subsequently, the airflow sounds may then be used as a waveform amplitude acoustic data stream in accordance with the forgoing method.

Figure 5:
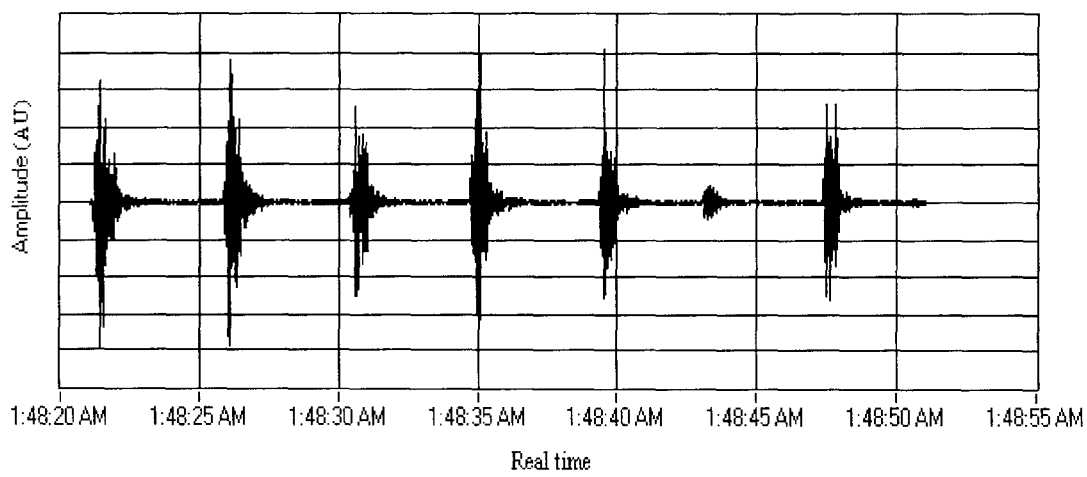
FIG. 5 is a digitized raw data wave plot representative of breathing sound amplitude versus time.

A raw acoustic data stream of breathing sounds, as shown in a representative plot, for example in FIG. 5, is then collected for each of a plurality of respiratory phases to form a bioacoustics signal recording, wherein the acoustic data stream is subsequently transformed.

As will be described below, in at least one embodiment, a method and an apparatus are provided to monitor, identify and determine the inspiratory and/or expiratory phases of the respiratory cycle of an individual 20 from the frequency characteristics breathing sounds. It is understood that a numerical comparative analysis of the frequency spectrum as transformed from waveform amplitude data of breathing sounds and/or airflow sounds of an individual 20 may be useful to differentiate between the inspiration and expiration phases of breathing.

Data Acquisition

Data were collected from 10 consecutive men and women at least 18 years of age referred for overnight polysomnography (PSG). The subjects' characteristics are shown in Table 1.

Breath sounds were recorded by a cardoid condenser microphone (Audi-Technica condenser microphone. Model PRO 35x). The microphone's cardioid polar pattern reduces pickup of sounds from the sides and rear, improving isolation of the sound source. The microphone 12 used for recording breath sounds has a relatively flat frequency response up to 2000 Hz as shown in FIG. 1. Furthermore, the microphone 12, as used herein has a higher output when sound is perpendicular to the microphone's diaphragm as shown by the solid line in FIG. 1, which helps reduce low frequency ambient noise interference. The microphone 12 was embedded in the centre of a loose fitting full face mask 16 modified to reduce airflow resistance and eliminate dead space by way of large openings 14 as shown in FIGS. 2a and 2b. The microphone 12 attached to the face mask 16, and was is located in front of the individual's face. The mask 16 provides a structural frame portion to keep the microphone in a fixed location, at a dimension A of approximately 3 cm in front of the individual's face, so as to record breathing sounds to an audio recording device, such as a computer as described above, to make an audio recording thereof. In some exemplary embodiments, the audio recording of breathing sounds may be made and recorded in analog format prior to digitizing the audio recording. However, in other embodiments the audio recording of breathing sounds may be digitized in real-time. Furthermore, in some exemplary embodiments, the processing of the audibly recorded waveform data or acoustic signal data may be performed in real-time, so as to provide substantially instantaneous information regarding an individuals breathing. In an exemplary embodiment, digitized sound data were transferred to a computer using a USB preamplifier and audio interface (M-Audio, Model MobilePre USB) with a sampling rate of 22,050 Hz and resolution of 16 bits. Although various types of audio interfaces may be used, in the instant exemplary embodiment, an external audio interface was preferred over a built-in audio adapter due to the better signal to noise (S/N) ratio of the external audio interface, which was 91 dB. FIG. 5 shows a 25-second waveform amplitude recording plot. However, in other exemplary embodiments, it may be desirable to record breathing sounds for a time period of from about 10 seconds to 8 hours. In some exemplary embodiments it may be desirable to record breathing sounds for a time period of from about 10 second to about 20 minutes. In other exemplary embodiments, it may be desirable to record breathing sounds for greater than 20 minutes.

Breathing Acoustics Analysis

In an exemplary embodiment, full night breath sound recordings were displayed on a computer screen similar to the computer screen 1.2 of FIG. 3. A representative raw acoustic data waveform plot, as may be shown on a computer screen 1.2, is provided in FIG. 5 for a 25-second recording. Each increase in amplitude represents a single breath. The individual phases of a breathing cycle are not readily resolvable in FIG. 5 owing to the time scale being too large to resolve single breath details. For example, FIG. 7a more clearly shows the inspiration and expiration phases of a breathing cycle in a waveform amplitude versus time plot. The recordings were visually scanned to identify periods of regular breathing. After visual scanning, the recordings were played back for auditory analysis.

Sequences of normal breaths that did not have signs of obstructive breathing such as snoring and interruptions, or other irregularities such as tachypnea (rapid breathing), or hyperventilation (deep breathing) were then included in the subsequent frequency analysis. This process was repeated to select three random parts of an individual's sleep. If a portion of the recording fulfilled the aforementioned inclusion criteria, then 3 to 4 consecutive breaths were selected from that portion. A total of 10 breaths were selected from each individual. During the process of selecting the individual's breathing sound portions, the investigator did not have a previous knowledge of the sleep stage. Therefore, the investigator was blind to the sleep stage of an individual while selecting the analyzed breaths except for knowing that sampling started after the onset of sleep. The real-time stamp of each breath was registered in order to retrieve the sleep stage in which it took place in afterwards. Subsequently, the investigator listened to these breathing sounds again to divide each breath into its inspiratory, expiratory and interbreath phases. Each phase was labeled manually.

The data array of each breathing phase was passed through a hamming window and a 2048-point Fast Fourier Transform (FFT) of the windowed data with 50% overlap was calculated. The resultant frequency spectrum was displayed on a computer screen for visual analysis. The frequency spectra of the interbreath pauses were also calculated and incorporated in the analysis to control for the effect of ambient noise. Careful visual examination of spectra revealed that during inspiration, the amplitude of signals above 400 Hz was consistently higher than during expiration. Therefore, it was determined that the bands ratio (BR) of frequency magnitude between 400 to 1000 Hz, to frequency magnitude between 10 to 400 Hz is higher in the inspiration phase as compared to the expiration phase. The BR of each breathing cycle was then calculated using equation (1).

$$BR = \sum_{400 Hz}^{1000 Hz} FFT(f) \bigg/ \sum_{10 Hz}^{400 Hz} FFT(f) \tag{1}$$

Using equation (1), the numerator represents the sum of FFT higher frequency magnitude bins which lie between 400 and 1000 Hz, and the denominator represents the sum of FFT lower frequency magnitude bins which lie between 10 and 400 Hz. Bins bellow 10 Hz were not included to avoid any DC contamination (referring to drift from a base line), and frequencies above 1000 Hz were not included since preliminary work (not shown) revealed insignificant spectral power at frequencies above 1000 Hz. Therefore, the computation may also be reduced. To verify repeatability of the results, BR was calculated for 3 to 4 successive breaths in the included sequence and for a total of three sequences from different parts of the individual's sleep. A total of 100 breaths were collected from the 10 subjects. The mean number of breaths per subject was 10±0.

Sleep Staging

Sleep stages were recorded during the course of the night using standard polysomnographic techniques that included electro-encephalography (EEG), electro-oculography and submental electro-myography (Rechtschaffen A and Kales A 1968 *A Manual of Standardized Terminology, Techniques and Scoring System for Sleep Stages of Human Subjects*. (Los Angeles: UCLA Brain Information Service/Brain Research Institute). The corresponding sleep stage for the selected breath samples was determined from the PSG recording (not shown).

Statistical Analysis

Data are expressed as mean±SD unless otherwise stated. A Wilcoxon Signed Ranks Test was performed using SPSS statistical package (SPSS, Chicago, Ill.). This test compares two related variables drawn from non-normally distributed populations. One-sample sing test was performed using Minitab 15 statistical package (Minitab Inc., State College, Pa.).

Comparison of Bands Ratio to Respiratory Inductance Plethysmography Subjects

Healthy subjects at least 18 years of age were recruited with no history of respiratory or cardiopulmonary disease in addition to being free from prescribed medications. Data were collected from 15 subjects. 6 men and 9 women, healthy volunteers. Individuals used in the study were recruited by advertisement and were divided randomly intro 2 groups with 5 subjects in one group (test group) and 10 in the other (validation group). The data from the 5 subjects in the test group were used to examine acoustic characteristics of breathing phases, which were then incorporated into a method having an algorithm as described below. The resultant method was tested on the data of 10 subjects in the validation group to determine the validity of the method for determining the inspiration and expiration phases of an individual's breathing sounds.

Breath Sound Recording

Breath sounds were recorded using a unidirectional, electret condenser microphone (Knowles Acoustics. Model MB6052USZ-2). The microphone's unidirectional pattern reduces the pickup of sounds from the sides and rear thereby improving isolation of the sound source. The microphone 12 was embedded in a respiratory mask 16 that was modified by cutting away material so as to produce opening 14 such that only a structural frame remained to keep the microphone 12 in a fixed location relative the nostrils and the mouth of an individual 20 at a dimension "A" of approximately 3 cm in front of the individual's face as shown in FIG. 2a. The audio signal was digitized using an audio signal digitizing module and digitized sound data were transferred via transducing link 18 to a computer using a USB preamplifier and audio interface (M-Audio, Model Fast Track Pro USB) with a sampling rate of 22,050 Hz and resolution of 16 bits. Although various types of audio interfaces may be used, in the instant exemplary embodiment, an external audio interface was preferred over the other types of audio adapters, for example, built-in audio adapters due to the superior signal to noise (S/N) ratio of the external adaptor which was about 60 dB at 1 kHz. Sound recordings were then passed through a $4^{th}$ order bandstop digital filter with a centre frequency of about 60 Hz to suppress line interference.

Respiratory Inductance Plethysmography

Respiratory inductance plethysmography (RIP). (Respitrace Ambulatory Monitoring Inc. White Plains, N.Y. USA) was used to monitor respiratory pattern of individuals and the timing of the breathing phases. In contrast to other breathing monitoring apparatus such as pneumotacography. RIP has the advantage of being applied away from the face of an individual to allow capture of breathing phases. Briefly, RIP is a system comprising two flexible sinusoidal wires. Each wire is embedded in stretchy fabric band. One band 28 is placed around the chest of an individual and the other band 30 is placed around the abdomen of the individual as shown in FIG. 6a. The inductance of each band changes upon rib cage and abdomen displacements and generates a voltage signal proportional to its inductance. The signals from the RIP bands 28 and 30 were digitized at 150 Hz and stored in a computer memory as substantially describe above with reference to FIGS. 3 and 4. The electrical sum of the ribcage and abdominal signals is displayed on a readable medium, for example a computer screen or a physical plot, and provides the total thoracoabdominal displacement. The thoracoabdominal displacement recorded from the RIP system reflects changes of tidal volume during respiration.

In order to compare the inspiration and expiration phases of an individual's breathing to RIP, the microphone 12, as noted above, was coupled to a modified mask 16 in front of the subject's face. Simultaneously, the RIP bands 28 and 30 were placed around the subject's chest and abdomen to measure thoracoabdominal motion as noted above. Recording were captured from both the microphone 12 and the RIP bands 28 and 30 simultaneously to assess the timing of breath sounds against the RIP waveform data.

Study Protocol

Individuals were studied in the supine position and were instructed to breathe normally. Microphone holding frame 16 was placed on individual's face. Each individual was asked to breath for two minutes at their regular breathing rate. In order to mimic all possible breathing conditions, the individuals were asked to breath through their nose only for half of the experiment time, and through their nose while mouth was slightly open in the other half. Incomplete breaths at the beginning and end of recording were discarded and all the breaths in between were included in the analysis.

Analysis of Breath Acoustics

In a first stage, spectral variables of breath sounds that characterize the inspiratory and expiratory phase components of a respiratory cycle were determined. The data of five subjects, 3 females and 2 males was chosen randomly from total 15 subjects and used to study the frequency characteristics of the acoustic signals of different respiratory phases. Inspiratory and expiratory segments of breath sounds were determined and extracted from the acoustic data by comparing it to the inspiratory (rising edge) and expiratory (falling edge) of the RIP trace as shown in FIG. 6b. A 25-second long recording of breath sounds and simultaneous summed thoracoabdominal RIP signals from a representative subject is shown, for example, in FIG. 6b. Dashed vertical lines are shown to separate inspiration and expiration phases of the second cycle at 32.

The first 10 complete breaths of each subject were analyzed, which yielded a total of 50 inspirations and 50 expirations acoustic data sets from the 5 subjects. Subsequently, the frequency spectrum of each phase was calculated separately using Welch's method (i.e. the average of a 2048-point Fast Fourier Transform (FFT) of sliding hamming windows with 50% overlap). FFT arrays were normalized in amplitude in order to compare the relative changes in power spectrum among resultant spectral arrays.

Using variables derived from frequency spectra of the 5 test individual's noted above, the inspiratory and expiratory phases of the breathing cycle were determined for the remaining 10 individuals in order to test the validity of the method. Furthermore, the method was tested for the ability to determine breathing phases from acoustic data independently from other inputs. The data analysis was performed with Matlab R2007b software package (Mathworks, Natick, Mass.).

Results

The characteristics of the individuals in this study are shown in Table 1. A total of 100 breaths were sampled from 10 patients with a mean number of 10 breaths per subject. Seventy percent of the breaths analyzed were from non-rapid-eye movement sleep (NREM), and 18% from rapid eye movement sleep (REM), and 12% while patients were awake according to the polysomnographic criteria.

TABLE 1

Characteristics of subjects.

| Subject | Age (years) | Sex | Body Mass Index |
|---|---|---|---|
| Subject 1 | 51 | F | 39.1 |
| Subject 2 | 43 | M | 25.6 |
| Subject 3 | 49 | M | 23.7 |
| Subject 4 | 27 | M | 36.8 |
| Subject 5 | 64 | M | 26.3 |
| Subject 6 | 60 | M | 33.0 |
| Subject 7 | 68 | F | 28.5 |
| Subject 8 | 31 | M | 30.3 |
| Subject 9 | 48 | F | 31.6 |
| Subject 10 | 56 | M | 26.7 |

Figure 7A:
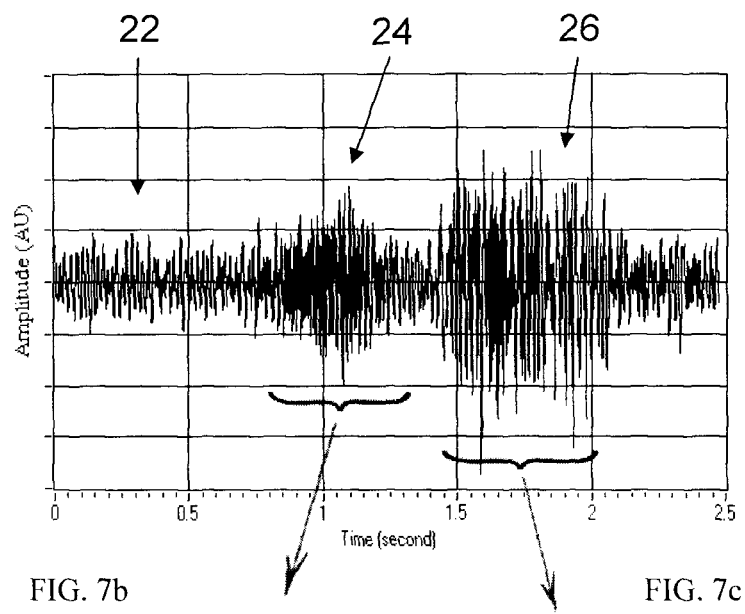
FIG. 7a is a representative digitized raw data breathing sound amplitude versus time plot of a single breathing cycle with the three phases of respiration.

The bands ratio (BR) value was calculated for the inspiration phase bands ratio (BRi) 24, the expiration phase bands ratio (BRe) 26, and the interbreath pause bands ratio (BRp) 22 using equation 1. Inspiration and expiration showed consistent patterns of their frequency spectra as depicted in FIG. 7a for a given breathing cycle.

Figure 7B:
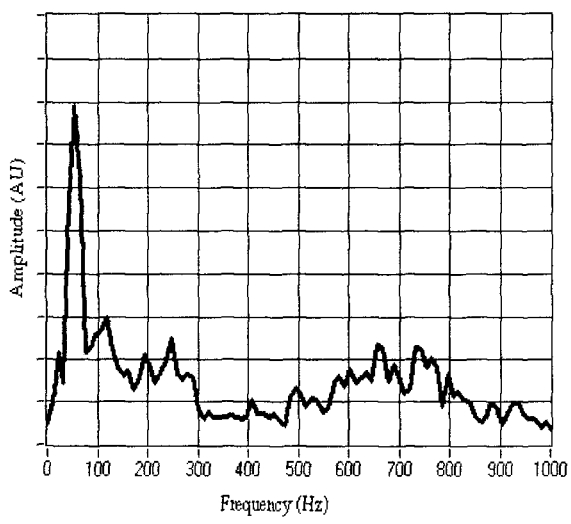

As shown in a representative example in FIG. 7b, there was a sharp narrow band of harmonics usually below 200 Hz for inspiration. The spectrum exhibited a valley between 200 Hz and 400 Hz and a peak again after 400 Hz as shown in FIG. 7b. Another variation of the inspiratory spectrum was the same initial narrow band followed by a relatively smooth spectrum without the 400 Hz drop (not shown). The expiratory spectrum, as shown in a representative example in FIG. 7c, on the other hand, formed a wider band that spanned frequencies up to 500 Hz and whose power dropped off rapidly above this frequency. The inspiratory spectrum (FIG. 7b) showed a peak close to the line frequency. The spectrum of the interbreath pause (not shown) was inconsistent and showed random variations without any consistent pattern. To rule out the effect of line frequency on inspiration bands ratio (BRi), a Wilcoxon signed rank test was used to test the relation between BRi and bands ratio interbreath pause (BRp). The test was significant ($p<0.001$), thus it was determined that BRi is different from BRp and that line interference does not significantly contribute to the frequency spectrum of inspiration.

The relationship between BRi and BRe was examined using the Wilcoxon Signed Ranks Test. The test showed that a BRi is not equal to BRe ($P<0.001$) with 95% of breathes having BRi greater than BRe. Since minute differences between BRi and BRe might be attributed to randomness, two thresholds of 50% and 100% difference between BRi and BRe were tested. The ratio BRi/BRe was calculated for each breath. By taking the ratio, BRi and BRe may be treated as dependant pairs. These ratios were then tested for being greater than 1.5 (50% difference) and greater than 2 (100% difference). The one-sample sign test showed that BRi/BRe is greater than 1.5 ($p<0.001$) and greater than 2 ($p<0.001$). In order to account for potential differences between subjects in the analysis, the mean BRi/BRe was calculated for each individual subject as displayed in Table 2. The one-sample sign test of the median was significant for mean BRi/BRe greater than 1.5 ($p=0.001$) and significant for mean BRi/BRe greater than 2 ($p=0.001$). Breaths that were drawn when subjects were polysomnographically awake did not differ significantly in terms of BRi/BRe from the rest of breaths ($p=0.958$) and, therefore, were included in the aforementioned analysis.

TABLE 2

Mean BRi/BRe for the subjects.

| Subject | Mean BRi/BRe (value ± SD) |
|---|---|
| Subject 1 | 1.66 ± 0.60 |
| Subject 2 | 2.30 ± 1.33 |
| Subject 3 | 2.43 ± 0.71 |
| Subject 4 | 3.17 ± 1.17 |
| Subject 5 | 2.67 ± 1.60 |
| Subject 6 | 3.86 ± 2.65 |
| Subject 7 | 23.01 ± 9.65 |
| Subject 8 | 14.99 ± 8.86 |
| Subject 9 | 15.66 ± 9.42 |
| Subject 10 | 11.56 ± 2.60 |

The sensitivity of this method was tested for each of the two cut-offs. Out of 100 breath samples, 90 had BRi 50% greater than BRe, and 72 had BRi 100% greater than BRe thereby giving an overall sensitivity of 90% and 72% respectively.

A total of 346 breaths met the inclusion criteria. The average number of breaths per individual was 23.0±7.79. Only the first 10 complete breaths were used to study the spectral frequency characteristics from the 5 individuals in the test group. From the validation group 218 breaths (i.e. 436 phases) were included in the analysis with an average of 21.8±8.2 breaths per subject.

Analysis of Breath Sounds

Figure 8A:
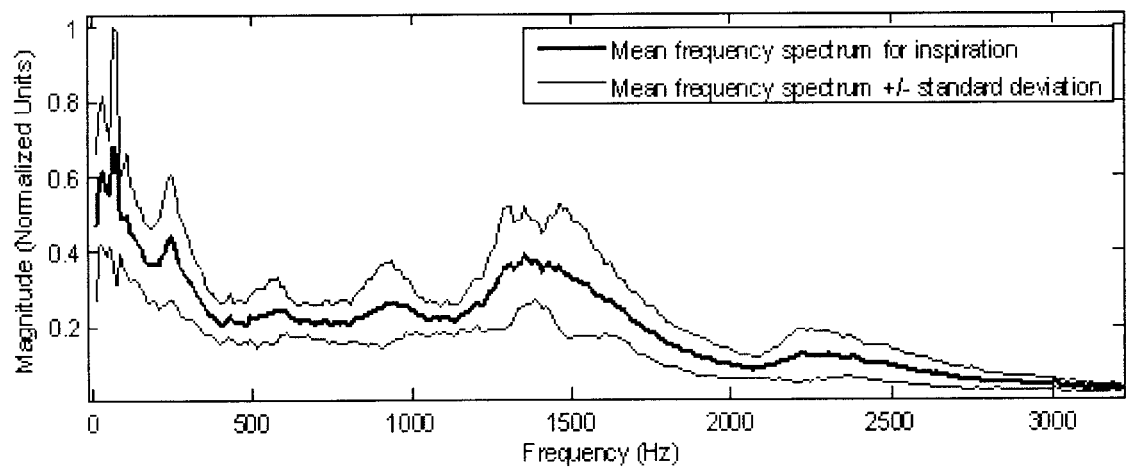
FIG. 8a is a representative plot of the average frequency magnitude spectrum and standard deviations of breathing sounds for inspiration in an individual.
Figure 8B:
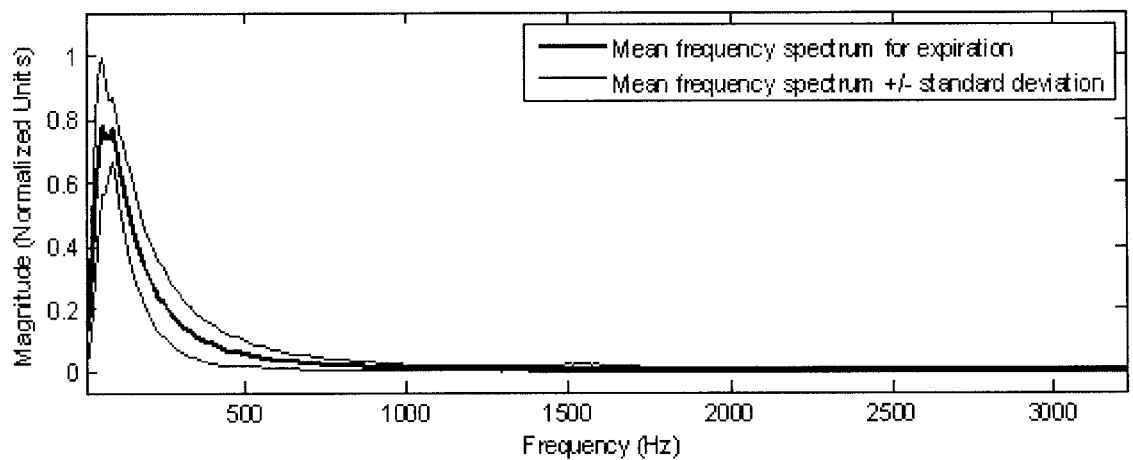
FIG. 8b is a representative plot of the average frequency magnitude spectrum and standard deviations of breathing sounds for expiration in an individual.

Data obtained from the test group of 5 individuals yielded 100 arrays of FFT magnitude bins normalized in amplitude with one half being from inspiratory acoustic inputs or phases and the other half from expiratory acoustic inputs or phases. The average spectrum of all normalized arrays belonging to the inspiration and expiration phases with the corresponding standard deviation are shown in FIGS. 8a and 8b respectively. FIGS. 8a and 8b demonstrate that the frequency spectra of the 2 phases have different energy distributions. The mean inspiratory spectrum, shown in FIG. 8a peaked between 30 Hz and 270 Hz. The spectrum exhibited flatness between 300 Hz and 1100 Hz before the next major peak with a center frequency of 1400 Hz. The expiratory spectrum, on the other hand, peaked between 30 to 180 Hz as shown in FIG. 8b. Its power dropped off exponentially until 500 Hz after which it flattened at low power.

The signal power above 500 Hz was consistently higher in inspiration than expiration. Since the ratio of frequency magnitudes between 500 to 2500 Hz, the higher frequency magnitude bins, to frequency magnitude between 0 to 500 Hz, the lower frequency magnitude bins, is higher during the inspiration phase than during the expiration phase for each breathing cycle, frequency ratio can be used to differentiate the two phases of the breathing cycle. This ratio is presented in equation (2) as the frequency bands ratio (BR).

$$BR = \sum_{500 Hz}^{2500 Hz} FFT(f) \bigg/ \sum_{0 Hz}^{500 Hz} FFT(f) \qquad (2)$$

The numerator of equation (2) represents the sum of FFT higher magnitude bins between 500 to 2500 Hz, and the denominator represents the sum of FFT lower magnitude bins below 500 Hz. BR was calculated for each of the six curves shown in FIGS. 8a and 8b which include the curve of the mean and the positive and negative standards deviation for both inspiration and expiration. These results are presented in Table 3:

TABLE 3

BR calculated for inspiration and expiration spectra.

| Inspiration | BR | Expiration | BR |
| --- | --- | --- | --- |
| Mean inspiration spectrum | 2.27 | Mean expiration spectrum | 0.15 |
| Mean inspiration spectrum + Std | 2.34 | Mean expiration spectrum + Std | 0.21 |
| Mean inspiration spectrum − Std | 2.14 | Mean expiration spectrum − Std | 0.02 |

The numbers in Table 3 represent the BR which is a ratio calculated from various curves.

Table 3 shows that the mean BR for inspiration (BRi) is 15.1 times higher than mean BR for expiration (BRe). BRi is higher than that for BRe. For example, by comparing the two extremes, 'BR for mean inspiration −Std', and 'BR for mean expiration +Std', as noted in Table 3 and shown in FIGS. 8a and 8b, BRi may be 10.2 time greater than that for BRe. However, other predetermined multipliers may be acceptable for determining the inspiration and expiration phases of breathing. For example, the multiplier maybe from about 1 to about to about 20. Therefore, the frequency-based variable BR may be used to distinguish the various phases of a given breathing cycle.

Figure 9:
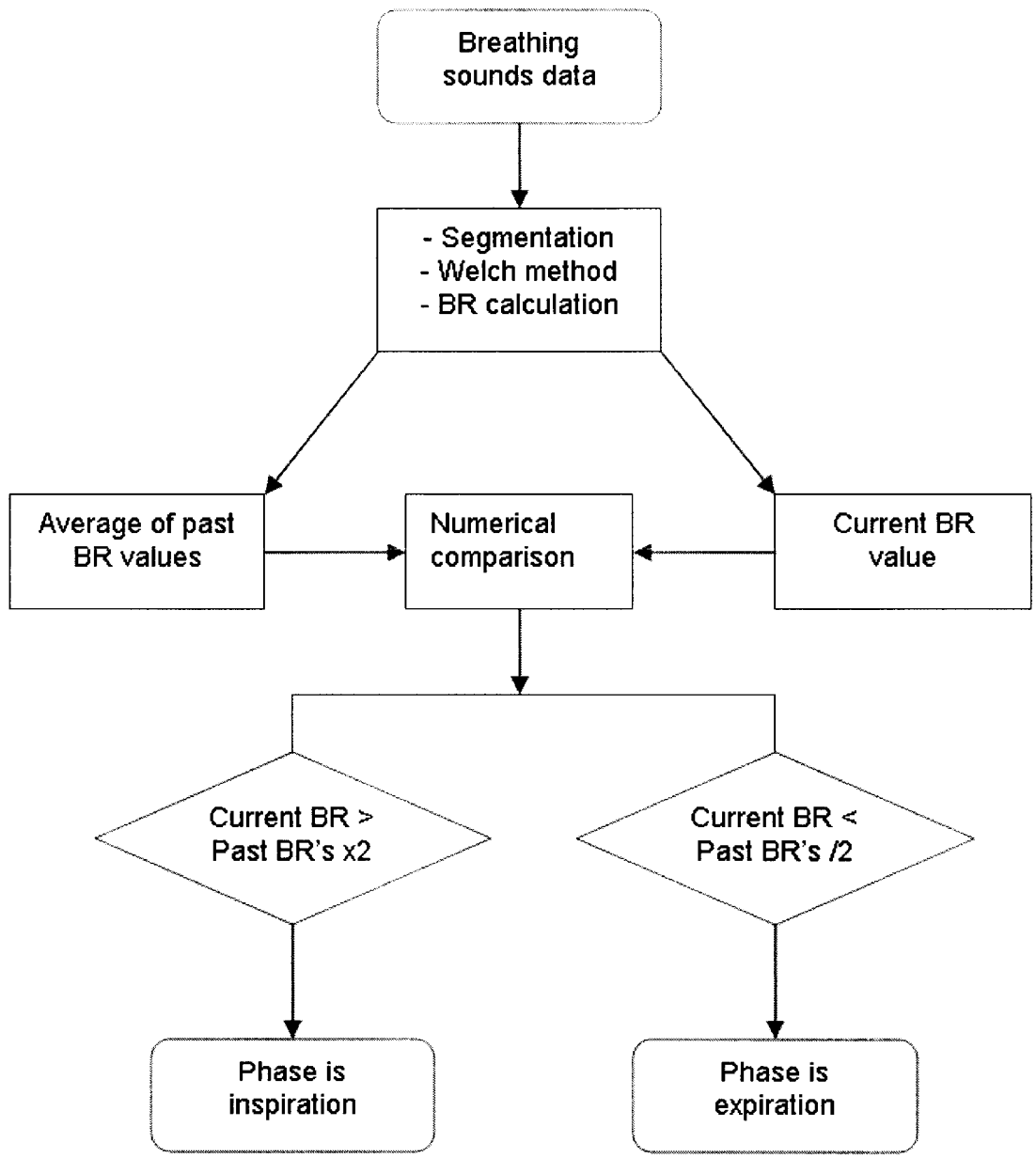
FIG. 9 is a flow diagram of the method for monitoring, identifying and determining the breathing phases from breathing sound data.
Figure 10A:
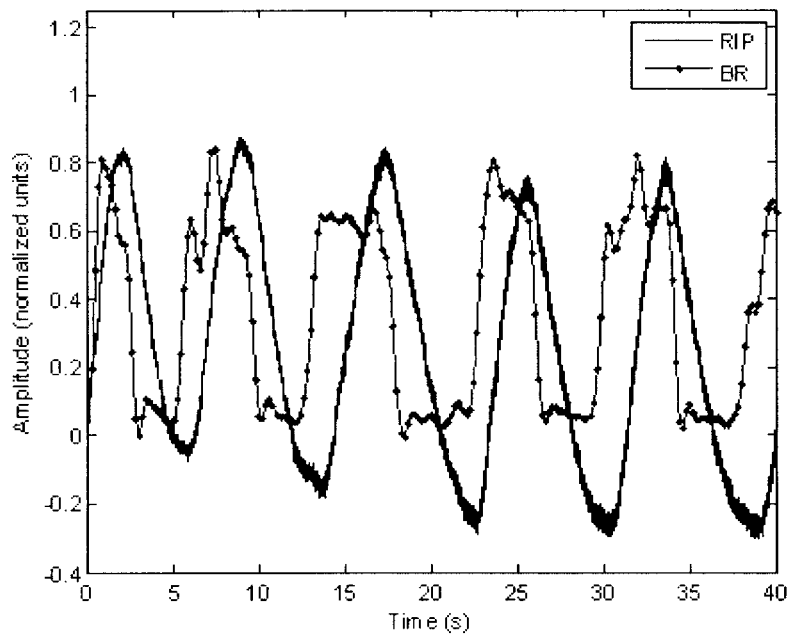
FIG. 10a is representative amplitude versus time plot of breathing sound data and simultaneous RIP data.
Figure 10B:
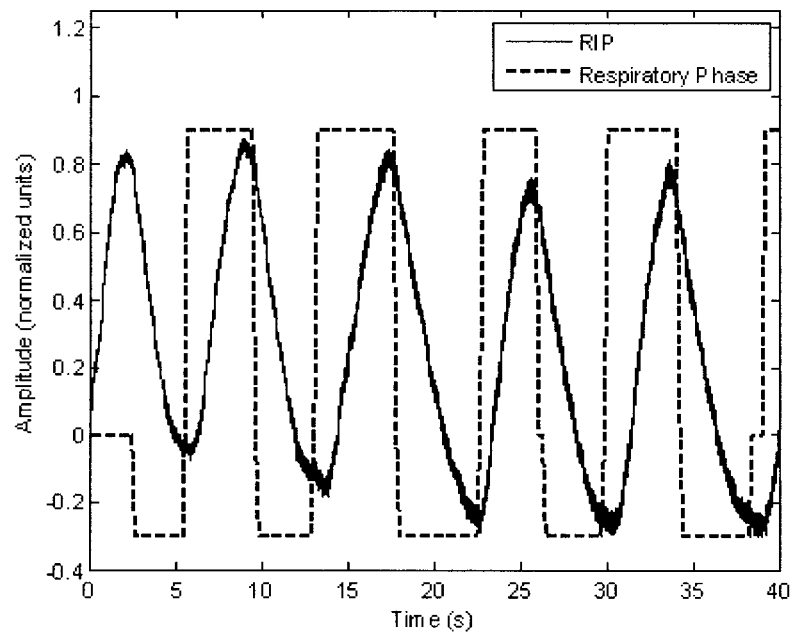
FIG. 10b is a comparative plot of the RIP data of FIG. 10a and the breathing phases found using the method of FIG. 9 for monitoring, identifying and determining breathing phases wherein the positive values of the dashed line represent inspiration and the negative values of the dashed line represent expiration.

In order to validate the results of the procedure as found using the test group, the BR parameters as determined above were utilized to track the breathing phases in the individuals in the validation group. A method that depends on past readings of acoustic data was developed to predict the current phase. A flow diagram of this method is shown schematically in FIG. 9. For example, a benefit of using past values rather than post-processed statistics is that the technique can be adopted for real-time implementation. According to this exemplary embodiment, the acoustic data stream is segmented into 200 ms segments. However, it may be desirable for the segments to be of a length greater than or less 200 ms. For example the segments may be from about 50 ms to about 1 second. Preferably, the segments are from about 100 ms to about 300 ms. Each segment is then treated as described above in relation to the test group. For example, Welch's method was applied to calculate frequency spectrum and it's BR, a first bands ratio (first BR). Subsequently the mean BR of the past 1.4 seconds (7 segments×200 ms) or the mean of all the past BR's, whichever is greater, was calculated. Each newly found BR, said first BR, was then compared with the past BR average or mean bands ratio. If the first BR is greater than the mean BR by at least a predetermined multiplier, then it is labeled as inspiration. The predetermined multiplier may be from about 1.1 to about 10. Preferably the multiplier is from about 1 to about 5. Most preferably, the multiplier is from about 1.5 to 2. For example, if the first BR is twice the past 1.4 seconds BR average (mean BR) then it is labeled as inspiration. Likewise, if the first BR is less than mean BR by at least a predetermined multiplier, then it is labeled as expiration. Therefore, for example, a segment is labeled as expiration if the corresponding BR is 2 times below the average of the past two segments. FIG. 10a shows an exemplary representative plot of an embodiment of all BR values calculated from the acoustic data with the corresponding RIP for comparison. Visual examination shows that there is a correlation between BR waveform and its RIP counterpart. Averaging of the BR's is performed in order to smooth out intra-phase oscillations in BR such as in the case of the BR curve at time 5-10 seconds seen in FIG. 10a The method was tested prospectively on the breathing acoustic data of 10 subjects in the validation group. The breathing phases found using the presently described method as applied to the data of FIG. 10a are shown in FIG. 10b. With reference to FIG. 10b, the dashed line represents the respiratory or breathing phases found utilizing the currently described method. Out of 436 breathing phases, 425 breathing phases were labeled correctly, 8 phases were partially detected, and 3 phases were labeled as being the opposite phases. Therefore, utilizing the method, about 97.4% of the breathing phases were detected correctly using acoustic data as compared with RIP trace.

With reference to FIG. 10b, the breathing cycles are shown as a processed wave amplitude versus time plot. The processed wave amplitude data are shown by the dashed line and indicate the respiration phase of an individual's breathing. In an exemplary embodiment, the processed wave amplitude versus time plot may be displayed on a display module such as that shown in FIG. 3 at 1.1. The processed wave amplitude versus time plot may also be, in some exemplary embodiments, provided to an operator by way of an information relay or relaying module in a printed form or other suitable form, for example audio cues, such that the breathing of an individual may be monitored in accordance with the method by an operator. In some exemplary embodiments, the information relay module may display or provide the processed data in terms or inspiration and/or expiration indicia.

The frequency spectrum of inspiration may be characterized by a narrow band below 200 Hz, a trough starting from about 400 Hz to about 600 Hz. In the exemplary embodiments noted herein, the trough begins at about 400 Hz in one, the first, embodiment (FIG. 7b) and at about 500 Hz in another, second, embodiment (FIG. 8a). A wider but shorter peak above may be seen at about 400 Hz to about 600 Hz. The peak is seen at about 400 Hz in the first embodiment (FIG. 7b) and at about 500 Hz in the second embodiment (FIG. 8a). In the embodiments noted herein, a smooth frequency distribution is noted after the decline of the initial narrow peak (FIGS. 7b and 8a). However, it maybe desirable in order embodiment to utilize various other frequencies and frequency ranges, for example by way of illustration and not limitation, greater than or less than about 400 Hz or 500 Hz.

Figure 7C:
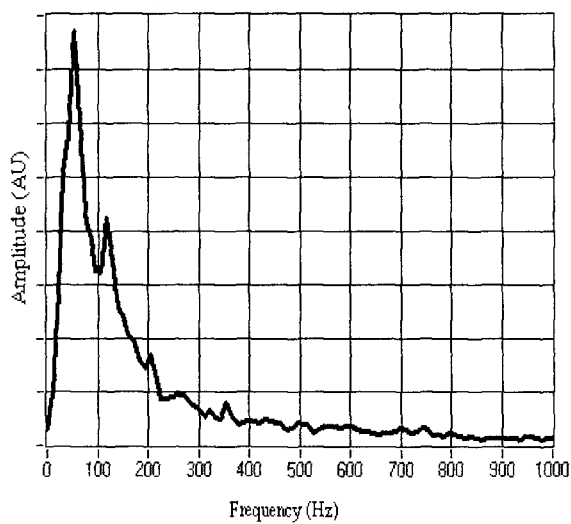

Expiration, on the other hand, may be characterized by a wider peak with a relatively sharp increase from about 10 to 50 Hz and a smooth drop from about 50 to 400 Hz as seen in the first embodiment shown in FIG. 7c or in the second exemplary embodiment as shown in FIG. 8b, above about 500 Hz. There is a relatively sparse frequency content above about 400 Hz in the first exemplary embodiment of FIG. 7c and likewise in the exemplary second embodiment of FIG. 8b above about 500 Hz. A cut-off point of 400 Hz in the first exemplary embodiment and 500 Hz in the second exemplary embodiment was chosen to distinguish between inspiration and expiration phases based upon these observations. Although recordings of breathing sounds have frequency content up to 10 kHz, most of the power lies below 2 kHz, and therefore higher frequencies may not be required to be considered. Additionally, frequencies below 10 Hz may also be excluded in order to avoid the effect of baseline shift (DC component). Therefore, a considering the aforementioned factors a simple ratio between the sums of magnitudes of bins of higher frequency (above about 400 Hz in the first embodiment and above about 500 Hz in the second embodiment) to those of lower frequency (about 10 Hz to about 400 Hz in the first embodiment and about 0 Hz to about 500 Hz in the second embodiment) distinguished the inspiration phase from the expiration phase of breathing. However, as the preceding embodiments are for exemplary purposes only and should not be considered limiting, other frequency ranges may be utilized. Additionally, the method may be fine tuned and/or modified as desired according to the location and type of the microphone.

As shown by way of the exemplary embodiments disclosed herein expiration may have a lower BR value than inspiration. Therefore the ratio of BRi/BRe for each breathing cycle was calculated in order to determine the intra-breath relationship between BRi and BRe. BRi/BRe was surprisingly found to be significantly greater than one. In other words, for each individual breath BRi is significantly higher than BRe. Since this exemplary method employs relative changes in spectral characteristics, it is not believed to susceptible to variations in overall signal amplitude that result from inter-individual variations.

The sensitivity of the exemplary method in certain embodiments is about 90% and 72% for 1.5-fold and 2-fold difference between the two phases respectively. However, there may be a trade-off between sensitivity and robustness; choosing a higher frequency cut-off may make the method more specific and less susceptible to noise but sensitivity may decrease.

As disclosed herein, a method for monitoring breathing by examining BR variables of short segments of breathing acoustic data is provided. The data was divided into 200 ms segments with subsequent Welch's method applied on each segment. However, longer or shorter segments may be desirable in various applications. The method involves applying FFT's on each segment and averaging the resultant arrays. Averaging FFT results within the segment further provides a random-noise-cancelling effect. The method of utilizing BRi/BRe in order to determine the breathing phase sound data a showed correlation with thoracoabdominal movement as seen in FIGS. 10a and 10b. Therefore, the currently provided method may be useful for monitoring, identifying and determining the breathing cycle phases of an individual. The method may, for example, be utilized for monitoring, identifying and determining the breathing phase from a pre-recorded audio track, or the method may also be utilized, for example for real-time monitoring of breathing.

For example, in a real-time breathing monitoring situations, BR variables may be examined in sequence and each BR variable is compared with a predetermined number of preceding BR values or preceding BR values. The preceding BR variables may be subject to a moving averaging window with the length of a breathing phase, which is approximately, for example 1.4 seconds. However, a longer or shorter window may be utilized as required. Although in one exemplary embodiment, there is shown a 10-15 fold difference in the BR between the breathing phases, a lower threshold may be considered. For example, since the moving averaging window incorporates transitional BR points between the inspiration and expiration phases which dilute the BR average of a pure breathing phase a greater or less fold-difference than that noted herein in the exemplary embodiments may be observed. Accordingly, an empirical threshold of 2 was chosen for the testing and illustration purposes of an example of the present method. Utilizing the method as provided herein, about 97.4% of the breathing phases were classified correctly.

The method and apparatus as defined herein may be useful for determining the breathing phases in sleeping individuals as well as being useful for determining the breathing phases of awake individuals. It provides a numerical method for distinguishing each phase by a comparison of segments of the frequency spectrum. The present exemplary method may, if desired, be used for both real-time and offline (recorded) applications. In both cases (online and offline) phase monitoring may be accomplished by tracking fluctuations of BR variables.

The present exemplary method may be applied to other applications which require close monitoring of respiration such as in intensive care medicine, anesthesia, patients with trauma or severe infection, and patients undergoing sedation for various medical procedures. The present exemplary method and apparatus provides the ability of integrating at least one microphone, and a transducing link with a medical mask thereby eliminating the need to attach a standalone transducer on the patients' body to monitor respiration. The present exemplary method may also be used for accurate online breathing rate monitoring and for phase-oriented inhaled drug delivery, for classification of breathing phases during abnormal types of breathing such as snoring, obstructive sleep apnoea, and postapnoeic hyperventilation.

Thus, the present method may thus be useful to classify breathing phases using acoustic data gathered from in front of the mouth and nostrils distal to the air outlets of an individual. A numerical method for distinguishing each phase by simple comparison of the frequency spectrum is provided. Furthermore, a method which employs relative changes in spectral characteristics, and thus it is not susceptible to variations in overall signal amplitude that result from inter-individual variations is provided and may be applied in real-time and recorded applications and breathing phase analysis.

The entire subject matter, of each of the references in the following list or otherwise listed hereinabove, is incorporated herein by reference:

Abeyratne U R, Wakwella A S and Hukins C 2005 Pitch jump probability measures for the analysis of snoring sounds in apnea *Physiological Measurement* 26 779-98

Arzt M, Young T, Finn L, Skatrud J B and Bradley T D 2005 Association of sleep-disordered breathing and the occurrence of stroke *Am J Respir Crit Care Med* 172 1447-51

Bieger-Farhan A K, Chadha N K, Camilleri A E, Stone P and McGuinness K 2004 Portable method for the determination of snoring site by sound analysis *Journal of Laryngology & Otology* 118 135-8

Bradley T D and Floras J S 2003 Sleep apnea and heart failure: Part 1: obstructive sleep apnea *Circulation* 107 1671-8

Campbell S S and Webb W B 1981 The perception of wakefulness within sleep *Sleep* 4 177-83

Duckitt W D, Tuomi S K and Niesler T R 2006 Automatic detection, segmentation and assessment of snoring from ambient acoustic data *Physiological Measurement* 27 1047-56

Fiz J A, Abad J, Jane R, Riera M, Mananas M A, Caminal P. Rodenstein D and Morera J 1996 Acoustic analysis of snoring sound in patients with simple snoring and obstructive sleep apnoea *European Respiratory Journal* 9 2365-70

Fiz J A, Jane R, Homs A, Salvatella D, Izquierdo J, Ruiz J, Caminal P and Morera J 1999 Wheezing identification in asthma subjects during forced exhalation *AMERICAN JOURNAL OF RESPIRATORY AND CRITICAL CARE MEDICINE* 159 A652

Folke M, Cernerud L, Ekstrom M and Hok B 2003 Critical review of non-invasive respiratory monitoring in medical care *Med Biol Eng Comput* 41 377-83

Guler E C, Sankur B, Kahya Y P and Raudys S 2005 Two-stage classification of respiratory sound patterns *Comput Biol Med* 35 67-83

Hill P D, Lee B W, Osborne J E and Osman E Z 1999 Palatal snoring identified by acoustic crest factor analysis *Physiological Measurement* 20 167-74

Hoffstein V, Mateika S and Anderson D 1994 Snoring: is it in the ear of the beholder? *Sleep* 17 522-6

Hult P, Fjallbrant T, Wranne B, Engdahl O and Ask P 2004 An improved bioacoustic method for monitoring of respiration *Technol Health Care* 12 323-32

Hult P, Wranne B and Ask P 2000 A bioacoustic method for timing of the different phases of the breathing cycle and monitoring of breathing frequency *Med Eng Phys* 22 425-33

Jane R. Cortes S, Fiz J A and Morera J 2004 Analysis of wheezes in asthmatic patients during spontaneous respiration *Conf Proc IEEE Eng Med Biol Soc.* 5 3836

Jane R, Fiza J A, Sola-Soler J, Blanch S, Artis P and Morera J Automatic snoring signal analysis in sleep studies. In: (2003). *Proceedings of the 25th Annual International Conference of the IEEE Engineering in Medicine and Biology Society* (IEEE Cat. No. 03CH37439) (pp. 366-9 Vol. 1). Piscataway, N.J.: IEEE. 4295 pp.; *Proceedings of the 25th Annual International Conference of the IEEE Engineering in Medicine and Biology Society*, 17-21 Sep. 2003, Cancun, Mexico. Whitaker Found, (USA p 366

Jane R, Sola-Soler J, Fiz J A and Morera J 2000 *Automatic detection of snoring signals: Validation with simple snorers and OSAS patients*

Jonathan Harrington and Cassidy S 1999 *Techniques in Speech Acoustics*: Kluwer Academic Publisher)

Rechtschaffen A and Kales A 1968 *A Manual of Standardized Terminology, Techniques and Scoring System for Sleep Stages of Human Subjects*. (Los Angeles: UCLA Brain Information Service/Brain Research Institute)

Leung R S and Bradley T D 2001 Sleep apnea and cardiovascular disease *Am J Respir Crit Care Med* 164 2147-65

Mattel A, Tabbia G and Baldi S 2004 Diagnosis of sleep apnea *Minerva Med* 95 213-31

Nieto F J. Young T B. Lind B K. Shahar E. Samet J M. Redline S, D'Agostino R B. Newman A B, Lebowitz M D and Pickering T G 2000 Association of sleep-disordered breathing, sleep apnea, and hypertension in a large community-based studs. Sleep Heart Health Study *Jama* 283 1829-36

Quinn S J, Huang L, Ellis P D and Williams J E 1996 The differentiation of snoring mechanisms using sound analysis *Clinical Otolaryngology & Allied Sciences* 21 119-23

Sankur B. Cagatay Guler E and Kahya Y P 1996 Multiresolution biological transient extraction applied to respiratory crackles *Comput Biol Med* 26 25-39

Sankur B, Kahya Y P, Guler E C and Engin T 1994 Comparison of AR-based algorithms for respiratory sounds classification *Comput Biol Med* 24 67-76

Sen I and Kahya Y 2005 A multi-channel device for respiratory sound data acquisition and transient detection *Conf Proc IEEE Eng Med Biol Soc.* 6 6658-61

Shahar E, Whitney C W, Redline S. Lee E T, Newman A 13. Javier Nieto F, O'Connor G T, Boland L L, Schwartz J E and Samet J M 2001 Sleep-disordered breathing and cardiovascular disease: cross-sectional results of the Sleep Heart Health Study *Am J Respir Cell Care Med* 163 19-25

Sola-Soler J, Jane R, Fiz J A and Morera J 2005 Variability of snore parameters in time and frequency domains in snoring subjects with and without Obstructive Sleep Apnea *Conf Proc IEEE Eng Med Biol Soc* 3 2583-6

Stock M., Kontrisova K., Dieckmann K., Bogner J., Poetter R., and Georg D., Development and application of a real-time monitoring and feedback system for deep inspiration breath hold based on external marker tracking, Medical physics. 33 (8) (2006) 2868.

Vegfors M, Lindberg L G, Pettersson H and Oberg P A 1994 Presentation and evaluation of a new optical sensor for respiratory rate monitoring *Int J Clin Monit Comput* 11 151-6

Wakwella A S, Abeyratne U R and Kinouchi Y 2004 Automatic segmentation and pitch/jitter tracking of sleep disturbed breathing sounds. In: (2004). 2004 *8th International Conference on Control, Automation, Robotics and Vision (ICARCV)* (IEEE Cat. No. 04EX920) (pp. 936-41 Vol. 2). Piscataway, N.J.: IEEE. 3 vol. (xxxiv+2341) pp.; 2004 *8th International Conference on Control, Automation, Robotics and Vision (ICARCV)*, 6-9 Dec. 2004, Kunming, China., (USA p 936

Yeginer M and Kahya Y 2005 Modeling of pulmonary crackles using wavelet networks *Conf Proc IEEE Eng Med Biol Soc* 7 7560-3

Young T, Evans L, Finn L and Palta M 1997 Estimation of the clinically diagnosed proportion of sleep apnea syndrome in middle-aged men and women *Sleep* 20 705-6

Young T, Palta M, Dempsey J, Skatrud J, Weber S and Badr S 1993 The occurrence of sleep-disordered breathing among middle-aged adults *N Engl J Med* 328 1230-5

Yu W., Baghaei H. Hongdi L., Yaqiang L., Tao X., Uribe J., Ramirez R., Shuping X., Soonseok K., and Wai-Hoi W. A simple respiration gating technique and its application in high-resolution PET camera, IEEE Transactions on Nuclear Science. 52 (1) (2005) 125.

While the present disclosure has been described for what are presently considered the preferred embodiments, the disclosure is not so limited. To the contrary, the disclosure is intended to cover various modifications and equivalent arrangements included within the spirit and scope of the appended claims. The scope of the following claims is to be accorded the broadest interpretation so as to encompass all such modifications and equivalent structures and functions.

The invention claimed is:

1. A computer-implemented method for monitoring a breathing cycle of an individual for classification of breathing phases during abnormal types of breathing, the breathing cycles including an inspiration phase and an expiration phase, the method automatically implemented by a computer processor to process an acoustic data stream of wave amplitude versus time, the data stream originating from breathing sounds captured from an individual, wherein the computer-implemented method comprises, via the processor:

segmenting the acoustic data stream plot into segments, each spanning a predetermined time period;

transforming the data stream so as to produce a frequency spectrum in each segment;

transforming the frequency spectrum in each segment so as to produce a plurality of magnitude of bins;

identifying a sample including a plurality of segments and determining therein a sum of lower frequency magnitude bins within a predetermined lower frequency range and a sum of higher frequency magnitude bins within a predetermined higher frequency range;

dividing the sum of higher frequency magnitude bins in the sampling by the sum of lower frequency magnitude bins so as to produce a mean bands ratio;

determining a sum of lower frequency magnitude bins and a sum of higher frequency magnitude bins within a given segment;

dividing the sum of higher frequency magnitude bins by the sum of lower frequency magnitude bins within said given segment so as to produce a first bands ratio; and determining if said first bands ratio is greater or less than said mean bands ratio by at least a predetermined multiplier; and digitally labeling said first bands ratio as inspiration if the first bands ratio is greater than the mean bands ratio by at least the predetermined multiplier;

digitally labeling said first bands ratio as expiration if the first bands ratio is lesser than the mean bands ratio by at least the predetermined multiplier; and outputting said breathing cycles as one of inspiration and expiration according to said labeling.

2. The method as defined in claim 1, wherein the predetermined multiplier is at least 1.

3. The method as defined in claim 1, the predetermined multiplier being greater than 1.5.

4. The method as defined in claim 1, the predetermined multiplier being greater than 2.

5. The method as defined claim 1, the breathing sounds being collected for a period of time of from about 10 seconds to about 8 hours.

6. The method as defined in claim 1, the breathing sounds being collected for a period of time of from about 10 seconds to about 20 minutes.

7. The method as defined in claim 1, the breathing sounds being collected for a period of time of from about 10 seconds to about 25 seconds.

8. The method as defined in claim 1, the breathing sounds being collected for a period of time of greater than 20 minutes.

9. The method as defined in claim 1, wherein the breathing sounds are collected for a period of time of about 25 seconds.

10. The method as defined in claim 1, each of the segments representing a time period of from about 50 ms to about 1 second.

11. The method as defined in claim 1, each of the segments representing a time period of from about 100 ms to about 500 ms.

12. The method as defined in claim 1, each of the segments representing a time period of about 200 ms.

13. The method as defined in claim 1, the lower frequency range being from about 0 Hz to about 500 Hz.

14. The method as defined in claim 1, the lower frequency range being from about 10 Hz to about 400 Hz.

15. The method as defined in claim 1, the higher frequency range being from about 500 Hz to about 25,000 Hz.

16. The method as defined in claim 1, the higher frequency range being from about 400 Hz to about 1,000 Hz.

17. The method as defined in claim 1, the sampling of the plurality of segments being selected from the recording randomly.

18. The method as defined in claim 1, the sampling of the plurality of segments including all of the segments in the recording.

19. The method as defined in claim 1, the mean bands ratio being determined from at least two segments preceding the first bands ratio segment.

20. The method as defined in claim 1, further comprising the breathing sounds with at least one microphone, and generating the acoustic data stream.

21. The method as defined in claim 20, the collecting of breathing sounds of the individual comprising airflow sounds resultant from the individual's breathing applying air pressure to a diaphragm of the microphone.

22. The method as defined in claim 20, the collecting of breathing sounds of the individual comprising actual breathing sounds sounds resultant from the breathing of the individual being recorded by the at least one microphone.

23. The method as defined in claim 20, the collecting of breathing sounds of the individual comprising airflow sounds resultant from the individual's breathing applying air pressure to a diaphragm of the at least one microphone and actual breathing sounds resultant from the individual being recorded by the at least one microphone.

24. The method as defined in claim 20, wherein the collecting of breathing sounds is digitized in real-time.

25. The method as defined in claim 20, wherein the processing of the collected acoustic data stream is performed in real-time.

26. The method as defined in claim 20, wherein the breathing sounds are collected by the at least one microphone including at least a first microphone and a second microphone;

the first microphone operable to collect breathing sounds and airflow sounds resultant from the individual's breathing applying air pressure to a diaphragm of the first microphone; and the second microphone operable to collect breathing sounds of the individual.

27. The method as defined in claim 20, the at least one microphone being provided in a structure including one or more openings of sufficient size to minimize airflow resistance and dead space.

28. An apparatus for transforming acoustic signal data of breathing sounds into a graphical representation indicative of breathing cycle phases including inspiration phases and expiration phases for classification of breathing phrases during abnormal types of breathing, comprising:

at least one microphone for collecting acoustic signal data resultant from the breathing of an individual during a given time period;

an acoustic signal data digitizing module for digitizing signal data to produce an acoustic data stream plot representative of wave amplitude versus time;

at least one processor operable for receiving the acoustic data stream plot, the processor configured for:

segmenting the acoustic data stream plot into a plurality of segments of a predetermined time period;

transforming the acoustic data stream in each of the plurality of segments so as to produce a plurality of frequency spectra wherein each frequency spectrum is representative of one of the plurality of segments;

transforming each frequency spectrum so as to produce a plurality of magnitude bins in each segment;

determining a sum of lower frequency magnitude bins within a predetermined lower frequency range and a sum of higher frequency magnitude bins within a predetermined higher frequency range within a sampling of the plurality of segments;

dividing the sum of higher frequency magnitude bins by the sum of lower frequency magnitude bins in the sampling so as to produce a mean bands ratio;

determining a sum of lower frequency magnitude bins and a sum of higher frequency magnitude bins within a given segment;

dividing the sum of higher frequency magnitude bins by the sum of lower frequency magnitude bins within said given segment so as to produce a first bands ratio; and comparing said mean bands ratio to said first bands ratio and determining if said first bands ratio is greater or less than said mean bands ratio by at least a predetermined multiplier so as to determine if said given segment is an inspiration phase or an expiration phase of the breathing cycle; and digitally labeling said first bands ratio as inspiration if the first bands ratio is greater than the mean bands ratio by at least the predetermined multiplier;

digitally labeling said first bands ratio as expiration if the first bands ratio is lesser than the mean bands ratio by at least the predetermined multiplier; and an information relay module in communication with the at least one processor for providing the transformed data to an operator as first indicia representing inspiration and expiration according to said labeling.

29. The apparatus as defined in claim 28, further comprising a sensor for sensing respiratory movements of an abdomen or rib region of the individual and generating a signal indicative thereof, the processor being operative to receive the signal and to identify respiratory expansion during inspiration and respiratory contraction during expiration, the information relay module being operable to provide data to an operator generated as second indicia representing the respiratory movements.

30. The apparatus as defined in claim 28, the information relay module being provided as a display module for displaying the transformed data as a processed wave amplitude versus time plot;

the inspiration phases being identifiable by rising regions of said processed wave amplitude versus time plot; and the expiration phases being identifiable by falling regions of said processed wave amplitude versus time plot.

31. The apparatus as defined in claim 28, the information relay module operable so as to provide an operator audio cues representing the inspiration and expiration phases of the individual's breathing.

32. The apparatus as defined in claim 28, the information relay module being provided as a display for displaying visual cues representing the inspiration and expiration phases of the individual's breathing.

33. The apparatus as defined in claim 28, the information relay module operable so as to provide an operator printed visual indicia representing the inspiration and expiration phases of the individual's breathing.

34. The apparatus as defined in claim 28, wherein the breathing sounds are collected by at least a first microphone and a second microphone;

the first microphone operable to collect acoustic signal data breathing sounds and airflow sounds resultant from the individual's breathing applying air pressure to a diaphragm of the first microphone; and the second microphone operable to collect acoustic signal data breathing sounds of the individual.

35. The apparatus as defined in claim 34, wherein the acoustic signal data collected by the second microphone are subtracted from the acoustic signal data collected by the first microphone so as to provide an acoustic signal data recording of airflow sounds of the individual.

36. The apparatus as defined in claim 28, the at least one microphone being provided in a structure including one or more opening sufficient to reduce airflow resistance and dead space.

\* \* \* \* \*